US011103891B2

(12) United States Patent
Sovic Brkicic et al.

(10) Patent No.: US 11,103,891 B2
(45) Date of Patent: Aug. 31, 2021

(54) PHARMACEUTICAL COMPOSITION

(75) Inventors: Ljiljana Sovic Brkicic, Zagreb (HR);
Zdravko Dokuzovic, Zagreb (HR)

(73) Assignees: Cvjetko Brkicic, Zagreb (HR);
Ljiljana Sovic Brkicic, Zagreb (HR)

( * ) Notice: Subject to any disclaimer, the term of this patent is extended or adjusted under 35 U.S.C. 154(b) by 714 days.

(21) Appl. No.: 14/009,996

(22) PCT Filed: Apr. 5, 2012

(86) PCT No.: PCT/EP2012/056366
§ 371 (c)(1),
(2), (4) Date: Feb. 12, 2014

(87) PCT Pub. No.: WO2012/136816
PCT Pub. Date: Oct. 11, 2012

(65) Prior Publication Data
US 2014/0154328 A1 Jun. 5, 2014

(30) Foreign Application Priority Data

Apr. 6, 2011 (EP) ................................. 11161398

(51) Int. Cl.
| A61K 9/50 | (2006.01) |
| A61K 47/48 | (2006.01) |
| B05D 1/22 | (2006.01) |
| A61K 9/48 | (2006.01) |
| A61K 31/198 | (2006.01) |
| A61K 47/58 | (2017.01) |
| A61K 9/20 | (2006.01) |
| A61K 45/06 | (2006.01) |
| B05D 1/02 | (2006.01) |

(52) U.S. Cl.
CPC .............. *B05D 1/22* (2013.01); *A61K 9/2081* (2013.01); *A61K 9/4808* (2013.01); *A61K 9/5026* (2013.01); *A61K 9/5047* (2013.01); *A61K 9/5073* (2013.01); *A61K 9/5084* (2013.01); *A61K 31/198* (2013.01); *A61K 45/06* (2013.01); *A61K 47/585* (2017.08); *B05D 1/02* (2013.01)

(58) Field of Classification Search
CPC .. A61K 9/5026; A61K 9/5073; A61K 9/5084; A61K 9/50; A61K 9/2081; A61K 9/4808; A61K 9/5047; A61K 47/585
See application file for complete search history.

(56) References Cited

U.S. PATENT DOCUMENTS

| 3,089,824 A | 5/1963 | Wurster |
| 3,117,027 A | 1/1964 | Lindlof |
| 3,253,944 A | 5/1966 | Wurster |
| 4,221,778 A | 9/1980 | Raghunathan |
| 4,361,545 A | 11/1982 | Powell |
| 4,832,957 A | 5/1989 | Dempski |
| 4,847,077 A | 7/1989 | Raghunathan |
| 4,859,461 A | 8/1989 | Chow |
| 4,859,462 A | 8/1989 | Chow |
| 4,900,755 A | 2/1990 | Dempski |
| 4,983,400 A | 1/1991 | Dempski |
| 6,001,392 A | 12/1999 | Wen |
| 2003/0224045 A1 | 12/2003 | Han |
| 2005/0181050 A1 | 8/2005 | Hirsh |
| 2007/0148238 A1 | 6/2007 | Nangia |
| 2008/0051459 A1 | 2/2008 | Nyholm |

FOREIGN PATENT DOCUMENTS

| CA | 1315690 C | * | 4/1993 |
| EP | 0294103 | | 12/1988 |
| EP | 0324947 | | 7/1989 |
| JP | S6335526 | | 2/1988 |
| JP | S63101332 | | 5/1988 |
| JP | H05132416 | | 5/1993 |
| JP | 2006513182 | | 4/2006 |
| JP | 2006515008 | | 5/2006 |
| JP | 2006522823 | | 10/2006 |
| KR | 19980015551 A | | 5/1998 |
| WO | 09406416 | | 3/1994 |
| WO | 09917745 | | 4/1999 |
| WO | 0101984 | | 1/2001 |
| WO | 2003020242 | | 3/2003 |
| WO | 2004067039 | | 8/2004 |
| WO | 2006081518 | | 8/2006 |
| WO | 2008064192 | | 5/2008 |
| WO | WO 2008151071 A1 | * | 12/2008 |

OTHER PUBLICATIONS

Goole et al., Levodopa delivery systems for the treatment of Parkinson's disease: An Overview, Intl. J. of Pharm., vol. 380, No. 1-2, pp. 1-15. Oct. 1, 2009.

* cited by examiner

Primary Examiner — Abigail VanHorn
Assistant Examiner — Mei Ping Chui
(74) Attorney, Agent, or Firm — Hodgson Russ LLP

(57) ABSTRACT

The invention relates to an oral pharmaceutical composition comprising coated particles of a complex of at least one active agent with an ion-exchange resin, wherein said particles are coated with a bioadhesive coating layer comprising at least one bioadhesive material. The invention also relates to a process for preparing the oral pharmaceutical composition.

25 Claims, 6 Drawing Sheets

PHARMACEUTICAL COMPOSITION

The present invention relates to oral pharmaceutical compositions providing controlled and site specific drug release.

BACKGROUND OF THE INVENTION

The controlled release of active agents is an important aspect in the oral administration of any drug. It is particularly important for the oral administration of active agents having narrow therapeutic windows. One example of such active agents is levodopa, the drug of choice in the treatment of Parkinson's disease.

Parkinson's disease (PD) is one of the most common neuro-degenerative diseases, which typically affect the elderly. Several classes of drugs have been utilized in the treatment of Parkinson's disease with varying degrees of success.

The prevalence of diagnosed PD in the population above the age of 55 is about 1.4% and it increases with age. Moreover, Parkinsonian signs in the elderly are estimated to occur in 30% of the population over the age of 65. Although PD is considered a multisystem disease, it is mainly a movement disorder caused by a continuous, long lasting degeneration of the dopaminergic neurons that are located in the mesencephalic substantia nigra pars compacta. PD becomes symptomatic only after degeneration of about 60-80% of these dopaminergic neurons, or after the loss of about 90% of the striatal dopamine. Dopamine, which is produced within the substantia nigra, normally reaches the striatum via the nigro-striatal tract and is released at the striatal synapses. Dopamine deficiency in the striatum, due to the degeneration of the dopaminergic neurons in the substantia nigra, is considered to be the cause of PD. However, dopamine itself is neither absorbed from the gastrointestinal tract nor able to pass across the brain-blood barrier.

Drugs comprising the natural metabolic dopamine precursor levodopa presently provide the most effective treatment of PD. Levodopa is capable of crossing the blood-brain barrier into the basal ganglia, where it is decarboxylated by the enzyme aromatic L-amino acid decarboxylase (AADC) to form dopamine, thereby replacing the missing neurotransmitter. However, AADC is also present in the gut wall, liver, kidney and cerebral capillaries, and the resulting peripheral decarboxylation of levodopa and formation of levodopa metabolites gives rise to a number of side-effects such as nausea, vomiting, cardiac dysrhythmias and postural hypotension. Peripheral levodopa decarboxylation can be largely prevented by additional administration of a selective extracerebral decarboxylase inhibitor, such as carbidopa or benserazide, which cannot itself pass the blood-brain-barrier. Levodopa combined with carbidopa or benserazide is now the treatment of choice when levodopa is indicated. Solid dosage forms containing a combination of levodopa and carbidopa are known and used to treat PD and other movement disorders. For instance, a rapid release oral tablet containing levodopa and carbidopa together with cellulose, magnesium stearate and starch is marketed under the name SINEMET®. However, even the levodopa/carbidopa combination therapy is often associated with severe side effects such as dyskinesias and psychiatric disturbances.

Moreover, the currently available preparations are effective only for a relatively short period and can be even deleterious under certain conditions. Using immediate release preparations of levodopa results in blood levels spikes with blood levels of levodopa that are initially too high and then soon afterwards too low to be effective. Moreover, only about 5% of the levodopa dose thus administered reaches the brain.

Involuntary movements (dyskinesias) in the form of orofacial or limb chorea or dystonia are common side effects of levodopa which often limit the possible dosage. Other side effects of levodopa include orthostatic hypotension, nightmares, hallucinations and, occasionally, toxic delirium. Hallucinations and delirium are most common in elderly, demented patients. In some patients, the drug cannot reduce Parkinsonism without producing some degree of dyskinesia or other side effects.

These side effects tend to occur at lower doses as treatment continues, and the so-called "wearing-off" and "on-off" phenomena have emerged as major problems in the levodopa long-term treatment of Parkinson's disease. After 2 to 5 years of treatment, >50% of patients begin to experience fluctuations in their response to levodopa. In most of these patients the benefit from each dose becomes shorter (the "wearing-off" effect) and some patients alternate unpredictably between mobility and immobility (the "on-off" effect). On periods are usually associated with high or rising plasma levodopa concentrations and often include abnormal involuntary movements, i.e. dyskinesias, and uncontrollable hyperactivity. "Off" periods have been correlated with low or falling plasma levodopa levels and bradykinetic episodes. Swings from on to "off" periods can occur many times a day. Traditionally, such swings have been managed by keeping individual doses of levodopa as low as possible and using dosing intervals as short as every 1 to 2 hours.

A number of techniques are generally known for formulating oral pharmaceutical compositions to control the release behavior of the pharmaceutically active agent. U.S. Pat. No. 4,221,778 describes prolonged continuous release pharmaceutical preparations containing an ion exchange resin having a pharmaceutically active drug adsorbed thereon to provide a drug/resin complex wherein at least a portion of the complex is treated with a solvating agent and provided with a diffusion barrier coating. U.S. Pat. Nos. 4,847,077, 4,859,461, 4,859,462 and 4,959,219 describe similar preparations using different solvating agents and plasticizers.

U.S. Pat. No. 6,001,392 describes a controlled-release antitussive syrup suspension for oral administration comprising a mixture of coated and non-coated cation exchange resins onto which dextromethorphan has been loaded, wherein about 30% of the drug/resin complexes are coated with a mixture of ethyl cellulose or ethyl cellulose latexes with plasticizers and water dispersible polymers.

U.S. Pat. No. 4,361,545 describes solid, orally administrable pharmaceutical compositions for the slow, zero order release of drugs having a water solubility of about 1/5-1/500 (w/w) which comprises a combination of a surface controlling compound having a water solubility of about 1/1-1/40 (w/w), an erosion controlling compound having a water solubility of about 1/1-1/10 (w/w), a surface activator and a surfactant.

WO 94/06416 A1 describes a pharmaceutical tablet consisting of a first layer containing one or more drugs with immediate or controlled release formulation, a second layer containing one or more drugs, either equal to or different from those of the first layer, with slow release formulation, and a low-permeability barrier-type layer coating said second layer or, alternatively, placed between the first and second layer.

Efforts have also been made to provide controlled release oral dosage combinations of levodopa and carbidopa.

U.S. Pat. Nos. 4,832,957, 4,900,755 and 4,983,400 describe a matrix or monolithic drug delivery system containing carbidopa and levodopa as active agents wherein the drugs are uniformly dispersed in a polymer vehicle at a concentration that is greater than either drug solubility in the polymer vehicle. The preferred vehicle is a combination of the water soluble polymer hydroxypropylcellulose and the less water soluble copolymer of polyvinyl acetate crotonic acid. Another preferred vehicle is polymethyl methacrylate.

US 2003/0224045 A1 describes a pharmaceutical dosage form comprising both immediate release and controlled release components comprising a combination of carbidopa and levodopa for the treatment of ailments associated with depleted amounts of dopamine in a patient's brain tissue.

WO 01/01984 A1 describes pharmaceutical compositions comprising levodopa, carbidopa and entacapone, and in particular an oral solid composition comprising pharmacologically effective amounts of levodopa, carbidopa and entacapone wherein a substantial amount of carbidopa is separated from entacapone and/or levodopa.

WO 99/17745 A1 describes a controlled-release monolithic system for oral administration comprising a disintegrating layer, an erodible layer and a swelling layer, of which two are external and one is intermediate, each layer containing one or more drugs such as levodopa and/or carbidopa.

A controlled release solid oral dosage formulation comprising levodopa and carbidopa in a polymer vehicle of hydroxypropylcellulose and polyvinylacetate-crotonic acid copolymer is marketed under the name SINEMET® CR.

The existing controlled release formulations comprising levodopa/carbidopa suffer from a number of disadvantages. In particular, these preparations typically exhibit a delayed onset. For example, the peak effect of the commercially available SINEMET® CR tablets was shown to occur one hour later than that of conventional SINEMET® tablets. Moreover, the bioavailability of existing controlled release formulations is low. At the same time, the clinical response to controlled release tablets was found to be less reliable and less predictable as compared to conventional formulations. Existing controlled release formulations of levodopa suffer from inadequate inter and intra patient reproducibility of blood levels. This is particularly problematic in the case of levodopa, where dosage often has to be increased over time to maintain efficacy, which further contributes to the development of long-term side effects.

In particular, it has been found that existing controlled release formulations of levodopa fail to provide a favorable effect comparable with continuous administration of levodopa such as via intravenous infusion. One the other hand, intravenous infusion of levodopa, in addition to being much less convenient for the patient, was found to frequently cause sclerosis of the peripheral veins.

US 2008/0051459 A1 describes a duodenal pump with intestinal administration of a composition comprising levodopa and optionally carbidopa continuously over a period greater than 16 hours. The clear disadvantage of this method of levodopa/carbidopa drug delivery is a need for a patient to have permanent duodenal or jejunal intubation, which is cumbersome, painful and prone to infections.

It is therefore an object of the present invention to overcome the disadvantages of the prior art and to provide an oral delivery system allowing for controlled and site specific release of drugs, and in particular drugs with narrow therapeutic windows such as levodopa and other drugs used in the treatment of Parkinson's disease and other movement disorders, to achieve maximal absorption, bioavailability, and optimal blood levels.

DESCRIPTION OF THE INVENTION

In one aspect the invention relates to an oral pharmaceutical composition comprising coated particles of a complex of at least one active agent with an ion-exchange resin, wherein said particles are coated with a bioadhesive coating layer comprising at least one bioadhesive material.

The composition according to the invention comprises at least one active agent. It will be understood that any such active agent is generally present in the composition in a therapeutically effective amount. The term "therapeutically effective amount" refers to an amount or quantity of active agent that is sufficient to elicit an appreciable biological response when administered to a patient.

All pharmacologically active agents are generally suitable for use in the composition of the invention. Preferred classes of active agents include antiparkinsonics, antiepileptics, antipsychotics, antidepressants, narcotics, antihypertensives, antioxidants, antineoplastics, cytostatics, gastrointestinal drugs and musculoskeletal drugs.

Examples of suitable active agents include ondansetron, granisetron, tropisetron, dolasetron, palonosetron, aprepitant, sulfasalazine, doxazosin, atenolol, bisoprolol, hydrochlorothiazide, carvedilol, amlodipine, felodipine, nifedipine, verapamil, diltiazem, enalapril, lisinopril, ramipril, quinapril, cilazapril, fosinopril, trandolapril, losartan, valsartan, simvastatin, lovastatin, fluvastatin, atorvastatin, rosuvastatin, gemfibrozil, fenofibrate, cholestyramine, oxybutynin, propiverine, solifenacin, trospium, darifenacin, sildenafil, phentolamine, tamsulosin, finasteride, cyclophosphamide, chlorambucil, melphalan, busulfan, lomustin, temozolomide, methotrexate, mercaptopurine, thioguanine, cladribine, fludarabine, cytarabine, 5-fluorouracil, gemcitabine, capecitabine, vinblastine, vincristine, vindesine, etoposide, paclitaxel, docetaxel, actinomycin D, doxorubicin, daunorubicin, epirubicin, idarubicin, mitoxantrone, bleomycin, mitomycin, cisplatin, carboplatin, oxaliplatin, procarbazine, rituximab, trastuzumab, cetuximab, bevacizumab, sunitinib, sorafenib, dasatinib, lapatinib, nilotinib, temsirolimus, amsacrine, asparaginase, hydroxyurea, estramustine, topotecan, irinotecan, imatinib, bortezomib, erlotinib, anagrelide, megestrol, tamoxifen, flutamide, nilutamide, bicalutamide, anastrazole, letrozole, exemestane, mycophenolate mofetil, sirolimus, everolimus, cyclosporine, tacrolimus, azathioprine, etidronic acid (e.g. etidronate sodium), clodronic acid (e.g. clodronate sodium), pamidronic acid (e.g. pamidronate sodium), alendronic acid (e.g. alendronate sodium), tiludronic acid (e.g. tiludronate sodium), ibandronic acid (e.g. ibandronate sodium), risedronic acid (e.g. risedronate sodium), zoledronic acid (e.g. zoledronate sodium), morphine, hydromorphone, oxycodone, pethidine, fentanyl, pentazocine, buprenorphine, tramadol, acetylsalicylic acid, metamizole, paracetamol, sumatriptan, methylphenobarbital, phenobarbital, primidone, phenyloin, ethosuximide, clonazepam, carbamazepine, oxcarbazepine, valproic acid, vigabatrin, progabide, tiagabine, sultiame, phenacemide, lamotrigine, felbamate, topiramate, gabapentin, pheneturide, levetiracetam, zonisamide, pregabalin, stiripentol, lacosamide, beclamide, trihexyphenidyl, biperiden, levodopa, carbidopa, benserazide, entacapone, amantadine, bromocriptine, pergolide, dihydroergocryptine, ropinirole, pramipexole, cabergoline, apomorphine, piribedil, rotigotine, selegiline, rasagiline, tolcapone, entacapone, budipine, levomepromazine, chlorpromazine, promazine, fluphenazine, perazine, haloperidol, sertindole, ziprazidone, zuclopenthixol, clozapine, olanzapine, quetiapine, loxapine, sulpiride, amisulpride, lithium (e.g. lithium carbonate), prothipendyl, risperidone, clotiapine, mosapramine, zotepine, aripiprazole, paliperidone, diazepam, alprazolam, meprobamate, flurazepam, nitrazepam, midazolam, zolpidem, clomipramine, amitriptyline, maprotiline, fluoxetine, citalopram, paroxetine, sertraline, alaproclate, fluvoxamine, etoperidon, escitalopram, mirtazapine, venlafaxine, methylphenidate, modafinil, neostigmine, pyridostigmine, disulfuram, naloxone, methadone, riluzole, abacavir, aciclovir, atropine, buspirone, caffeine, captopril, chloroquine, chlorphenamine, desipramine, diphenhydramine, disopyramide, doxepin, doxycycline, ephedrine, ergonovine, ethambutol, glucose, imipramine, ketorolac, ketoprofen, labetalol, levofloxacin, metoprolol, metronidazole, minocycline, misoprostol, phenazone, phenylalanine, prednisolone, primaquine, propranolol, quinidine, rosiglitazone, salicylic acid, theophylline, zidovudine, codeine, dextromethorphan, hydrocodone, hydralazine, metaproterenol, phenylpropanolamine and pseudoephedrine.

The composition of the invention is particularly suitable for active agents belonging to Class I of the Biopharmaceutics Classification System (BCS). BCS Class I active agents are characterized in exhibiting both high permeability and high solubility. Examples of BCS Class I active agents include abacavir, aciclovir, amitriptyline, atropine, buspirone, caffeine, captopril, chloroquine, chlorphenamine, cyclophosphamide, desipramine, diazepam, diltiazem, diphenhydramine, disopyramide, doxepin, doxycycline, enalapril, ephedrine, ergonovine, ethambutol, fluoxetine, glucose, imipramine, ketorolac, ketoprofen, labetalol, levodopa, levofloxacin, metoprolol, metronidazole, midazolam, minocycline, misoprostol, nifedipine, paracetamol, pethidine, phenazone, phenobarbital, phenylalanine, prednisolone, primaquine, promazine, propranolol, quinidine, risperidone, rosiglitazone, salicylic acid, theophylline, verapamil and zidovudine.

Active agents having short biological half-lives in the order of up to about 8 hours are also preferred. Examples include codeine, dextromethorphan, doxepin, ephedrine, hydrocodone, hydralazine, metaproterenol, morphine, levodopa, carbidopa, benserazide, entacapone, phenylpropanolamine, pseudoephedrine and verapamil.

Levodopa, carbidopa, benserazide, entacapone and mixtures thereof are particularly preferred.

The composition of the invention can comprise a combination of two or more active agents. Preferred combinations of active agents include bisoprolol/hydrochlorothiazide, verapamil/trandolapril, amlodipine/atorvastatin, tramadol/paracetamol, beclamide/trihexyphenidyl, buprenorphine/naloxone, levodopa/carbidopa, levodopa/benserazide and levodopa/carbidopa/entacapone.

Unless indicated otherwise, all references to active agents herein are meant to include pharmaceutically acceptable salts and solvates thereof. Such references are further meant to include both crystalline and amorphous forms. As used herein, the term "pharmaceutically acceptable" refers to materials that are suitable for use in humans and animals without excessive toxicity, commensurate with a reasonable benefit/risk ratio.

The composition of the invention comprises coated particles of a complex of at least one active agent with an ion exchange resin.

Suitable ion exchange resins are typically water-insoluble and comprise a pharmacologically inert organic or inorganic matrix containing covalently bound functional groups that are ionic or capable of being ionized under appropriate pH conditions. Examples of organic matrices include synthetic matrices (e.g. polymers or copolymers of acrylic acid, methacrylic acid, styrene sulfonate or divinylbenzene sulfonate) and partially synthetic matrices (e.g. modified cellulose or dextran). Examples of inorganic matrices include silica gel modified by the addition of ionic groups. The covalently bound ionic groups can be strongly acidic (e.g. sulfonic acid groups), weakly acidic (e.g. carboxylic acid groups), strongly basic (e.g. quaternary ammonium groups), weakly basic (e.g. primary amine groups) or a combination of acidic and basic groups. Ion exchange resins suitable for ion exchange chromatography or deionization of water are normally also suitable for use in the present invention. Such ion exchange resins are for instance described by H. F. Walton, "Principles of Ion Exchange" in E. Heftmann (Ed.), "Chromatography: A laboratory handbook of chromatographic and electrophoretic methods", 3rd ed., Van Nostrand, N.Y., 1975, pp. 312-343. Suitable ion exchange resins typically have exchange capacities below about 6 meq./g (milliequivalents per gram) and particularly below about 5.5 meq./g of dry resin (free acid or base form).

The ion exchange resin is preferably selected from the group consisting of polymers and copolymers of acrylic acid, methacrylic acid and styrene modified with ionic groups, cellulose modified with ionic groups, dextran modified with ionic groups and silica gel modified with ionic groups.

Suitable ionic groups include sulfonate groups, tertiary amine groups and quaternary ammonium groups. Polymers and copolymers of styrenesulfonate, styrylmethyltrimethylammonium salts and dimethylaminomethylstyrene are particularly preferred.

It is further preferred that the ion exchange resin is crosslinked with a crosslinking agent. Suitable crosslinking agents are generally known in the art. Preferred crosslinking agents are divinyl and polyvinyl compounds, most preferably divinylbenzene. The ion exchange resin is preferably crosslinked to an extent of about 3 to about 20 wt. %, particularly about 4 to about 16 wt. %, more preferably about 6 to about 10 wt. %, and most preferably about 8 wt. % based on the total weight of dry resin (free acid or base form).

It is particularly preferred that the ion exchange resin is a crosslinked sulfonated copolymer of styrene and divinylbenzene, which is preferably crosslinked to an extent of about 8 wt. % based on the total weight of dry resin ($H^+$-form). This ion exchange resin typically has an ion exchange capacity of about 4.5 to 5.5 meq./g of dry resin ($H^+$-form). Another preferred ion exchange resin is a crosslinked copolymer of styrene functionalized with quaternary ammonium groups and divinylbenzene, which is preferably crosslinked to an extent of about 8 wt. % based on the total weight of dry resin ($H^+$-form). This ion exchange resin typically has an ion exchange capacity of about 3 to 4 meq./g of dry resin ($H^+$-form).

The ion exchange resin preferably has an average particle size in the range of from about 10 to about 1000 µm, particularly in the range of from about 20 to about 250 µm, most preferably in the range of from about 25 to about 200 µm. The ion exchange resin can be in the form of irregularly shaped particles having an average particle size in the range of from about 40 to about 250 μm, or spherical particles having an average particle size in the range of from about 45 to about 150 μm.

It is further preferred that the complex of the at least one active agent with the ion-exchange resin comprises the active agent(s) in an amount of about 5 to 80 wt. %, particularly 10 to 70 wt. %, more preferably 20 to 60 wt. %, and most preferably 30 to 50 wt. %, based on the total weight of the complex.

The average particle size of the complex of the at least one active agent with the ion exchange resin is preferably about to 3000 μm, particularly about 30 to 2000 μm, and most preferably about 50 to 1000 μm. It is further preferred that at least about 85%, particularly at least about 95%, and most preferably at least about 98% by volume of the particles have an average particle size within these preferred ranges. As used herein, the term average particle size refers to the volume average. Particle size can be determined by sieve analysis or laser diffraction analysis as generally known in the art. Sieve analysis is typically performed on a dry powder sample. Laser diffraction analysis can be performed using a sample as dry powder or suspended in an inert liquid vehicle such as purified water for instance using a Malvern Mastersizer Apparatus MS 2000.

The coated particles further comprise a bioadhesive coating layer comprising at least one bioadhesive material. The term "bioadhesive" generally refers to a material which is capable of imparting adhesion of particles to a biological surface (e.g. tissue and/or cells) and in particular to a mucous membrane.

Suitable bioadhesive materials generally include modified and unmodified natural or synthetic hydrophilic homopolymers, copolymers and hydrogels. Examples include polycarboxylates, hyaluronan, chitosan, alginates such as sodium alginate, pectin, xanthan gum, poloxamers, cellulose derivatives, polyvinyl acetate and polyvinylpyrrolidone. Preferred are modified and unmodified synthetic polycarboxylate polymers, which typically have a weight average molecular weight of at least about 10,000 Daltons, preferably at least about 50,000 Daltons, more preferably at least about 100,000 Daltons, still more preferably at least about 1,000,000 Daltons, and most preferably from about 1,000,000 to about 10,000,000 Daltons. Modifications can include crosslinking, neutralization, hydrolysis and full or partial esterification.

Preferred bioadhesive materials include optionally crosslinked polymers and copolymers of acrylic acid or alkylacrylic acids, particularly optionally crosslinked copolymers of acrylic acid or methacrylic acid with $(C_{10}$-$C_{30})$alkyl acrylate. Suitable crosslinkers include vinyl and allyl ethers of polyalcohols, particularly allyl sucrose, allyl pentaerythritol and divinyl glycol. Homopolymers of acrylic acid crosslinked with allyl sucrose or allyl pentaerythritol and copolymers of acrylic acid and $(C_{10}$-$C_{30})$alkyl acrylate crosslinked with allyl pentaerythritol are particularly preferred.

It is further preferred that the bioadhesive coating layer is present in an amount of 1 to 30 wt. %, particularly 2 to 10 wt. % and more preferably 3 to 7 wt. % based on the combined weight of the complex, an optionally present release modifying coating layer and the bioadhesive coating layer.

The coated particles optionally comprise a release modifying coating layer which is placed between the complex and the bioadhesive layer and comprises at least one release modifying material. In certain embodiments, particularly if the active agent(s) belong to Class II or IV of the Biopharmaceutics Classification System (BCS), which active agents are characterized in exhibiting low solubility, the composition can consist exclusively of particles that do not comprise a release modifying coating layer. Preferably at least a portion of the coated particles comprise the release modifying coating layer. The release modifying material is preferably selected from delayed release materials and/or controlled release materials.

Suitable delayed release materials typically possess no or limited solubility or erodibility in a first environment, while being soluble and/or erodible in a second environment. Examples of suitable delayed release materials include anionic cellulose derivatives, anionic vinyl resins, anionic acrylic resins and combinations thereof. Preferred anionic cellulose derivatives include cellulose ethers, cellulose esters and cellulose ester-ethers, particularly alkylcelluloses, hydroxyalkylcelluloses, hydroxyalkylalkylcelluloses and acylcelluloses, which are esterified with di- or tricarboxylic acids. Cellulose acetate phthalate, cellulose acetate trimellitate, hydroxypropyl methylcellulose phthalate and hydroxypropyl methylcellulose acetate succinate are particularly preferred. Preferred anionic vinyl resins include polyvinylesters which are esterified with di- or tricarboxylic acids. Polyvinyl acetate phthalate is particularly preferred. Preferred anionic acrylic resins include polymers and copolymers of acrylic acid or alkylacrylic acid, particularly copolymers of acrylic or methacrylic acid with alkylacrylates or alkylmethacrylates. Poly(methacrylic acid-co-ethylacrylate) and poly(methacrylic acid-co-methylmethacrylate) are particularly preferred. Most preferred as delayed release materials are cellulose acetate phthalate, polyvinyl acetate phthalate, poly(methacrylic acid-co-ethylacrylate) 1:1, hydroxypropyl methylcellulose acetate succinate, poly(methacrylic acid-co-methylmethacrylate) 1:1, poly(methacrylic acid-co-methylmethacrylate) 1:2 and combinations thereof, and most preferably cellulose acetate phthalate, polyvinyl acetate phthalate, poly(methacrylic acid-co-ethylacrylate) 1:1, hydroxypropyl methylcellulose acetate succinate and combinations thereof.

Suitable controlled release materials generally include natural and synthetic film-forming materials having diffusion barrier properties. Such materials generally should be insoluble in water and permeable to water and active agent. However, it can be desirable to incorporate a water-soluble substance, such as methyl cellulose, to alter the permeability of the coating, or to incorporate an acid-insoluble, base-soluble substance to act as an enteric coating. Examples of suitable controlled release materials are also described by R. C. Rowe in "Materials used in Pharmaceutical Formulation", A. T. Florence (Ed.), Blackwell Scientific Publications, Oxford, 1984, pp. 1-36. Examples of suitable controlled release materials include cellulose derivatives such as cellulose ethers and cellulose esters, (meth)acrylic resins such as acrylate and methacrylate polymers and copolymers, vinyl resins such as polymers and copolymers of vinylpyrrolidone, vinylacetate and vinylchloride, shellac, zein, rosin esters, silicone elastomers and mixtures thereof. Preferred cellulose derivatives include alkylcelluloses, hydroxyalkylcelluloses, hydroxyalkylalkylcelluloses and acylcelluloses, particularly ethyl cellulose, methyl cellulose, hydroxypropyl methylcellulose and cellulose acetate. Preferred (meth)acrylic resins include acrylate and methacrylate copolymers optionally comprising quaternary amine functional groups, particularly poly(ethyl acrylate-co-methyl methacrylate) and poly(ethyl acrylate-co-methyl methacrylate-co-trimethylammonioethyl methacrylate chloride), more particularly poly(ethyl acrylate-co-methyl methacrylate) 2:1, poly(ethyl acrylate-co-methyl methacrylate-co-trimethylammonioethyl methacrylate chloride) 1:2:0.1 and poly(ethyl acrylate-co-methyl methacrylate-co-trimethylammonioethyl methacrylate chloride) 1:2:0.2. Preferred vinyl resins include polyvinylpyrrolidone, poly(vinylpyrrolidone-co-vinylacetate) and mixtures thereof. Ethyl cellulose, methyl cellulose and mixtures thereof are particularly preferred. Most preferably the controlled release coating comprises a water-based ethyl cellulose latex or pseudolatex plasticized with dibutyl sebacate or vegetable oils.

The release modifying coating layer is preferably present in an amount of from about 5 to about 70 wt. %, particularly about 10 to about 60 wt. %, and more preferably about 20 to about 50 wt. %, based on the combined weight of the complex and the release modifying coating layer. Variations in the amount of release modifying material and/or the use of mixtures of coated and uncoated particles can be employed to selectively modify the dissolution profile as desired. It is preferred that about 20 to about 80%, more preferably about 30 to about 70% and most preferably about 40 to about 60% of the particles comprise a release modifying coating layer.

According to a preferred embodiment, the composition comprises at least two groups of coated particles differing in the amount and/or the composition of release modifying material and/or comprising different active agents.

In one embodiment, the composition comprises a first group of coated particles comprising a release modifying layer and a second group of coated particles having no release modifying layer or having a release modifying layer with a lower amount of release modifying material. In another embodiment, the composition comprises two groups of coated particles comprising release modifying layers differing in the composition of the release modifying material. In these embodiments, those particles having no release modifying layer or having a release modifying layer with a lower amount of release modifying material will exhibit a faster release of active agent. Likewise, groups of particles differing in the composition of the release modifying material will exhibit different release behaviors.

When the composition comprises at least two different groups of coated particles, the active agent(s) of these groups of particles can be the same or different. When the active agent(s) are the same, the combination of different groups of coated particles exhibiting different release behavior can be used to adapt the overall release profile of the active agent. When the active agent(s) are different, the different active agents can be provided according to different release profiles, e.g. one active agent can be released faster and/or earlier than another active agent.

It will be appreciated that these and other embodiments can also be combined to provide compositions comprising any number of different groups of coated particles. For example, a composition in accordance with the invention can comprise a first group of coated particles comprising a first active agent or combination of active agents and a release modifying layer, a second group of coated particles comprising the same active agent or combination of active agents without a release modifying layer and a third group of coated particles comprising a different active agent or combination of active agents.

The coated particles optionally comprise an enteric coating layer which is placed over the bioadhesive layer and comprises at least one enteric coating material. The enteric coating layer is preferably placed directly over the bioadhesive layer, i.e. without another layer between the bioadhesive layer and the enteric coating layer. Suitable enteric coating materials are generally known in the art. They are typically substantially resistant to gastric juices so as to largely prevent release of active agent in the stomach and thus promote enteric release. Examples of suitable enteric coating materials include anionic cellulose derivatives, anionic vinyl resins, anionic acrylic resins.

Preferred anionic cellulose derivatives include cellulose ethers, cellulose esters and cellulose ester-ethers such as alkylcelluloses, hydroxyalkylcelluloses, hydroxyalkylalkylcelluloses or acylcelluloses, which are esterified with di- or tricarboxylic acids such as phthalic acid, hexahydrophthalic acid, trimellitic acid or succinic acid and pharmaceutically acceptable salts thereof. Cellulose ether phthalates, cellulose ester phthalates, cellulose ester-ether phthalates and pharmaceutically acceptable salts thereof are preferred. Particularly preferred are cellulose acetate phthalate, cellulose diacetate phthalate, cellulose triacetate phthalate, methylcellulose phthalate, hydroxypropyl cellulose phthalate, hydroxypropyl methylcellulose phthalate, cellulose acetate hexahydrophthalate, hydroxypropyl methylcellulose hexahydrophthalate and pharmaceutically acceptable salts thereof. Preferred pharmaceutically acceptable salts include alkaline, alkaline earth and ammonium salts, particularly sodium cellulose acetate phthalate, calcium cellulose acetate phthalate and ammonium hydroxypropyl methylcellulose phthalate.

Preferred anionic vinyl resins include polyvinylesters which are esterified with di- or tricarboxylic acids such as phthalic acid, hexahydrophthalic acid, trimellitic acid or succinic acid and pharmaceutically acceptable salts thereof. Polyvinyl acetate phthalate is particularly preferred. Even more preferred are mixtures of anionic vinyl resins with phthalate plasticizers such as dialkyl phthalates, e.g. diethyl phthalate or dibutyl phthalate, alkylaryl phthalates or diarylphthalates.

Preferred anionic acrylic resins include polymers and copolymers of acrylic acid or alkylacrylic acid, and in particular copolymers of acrylic or methacrylic acid with alkylacrylates or alkylmethacrylates. Examples include poly(methacrylic acid-co-ethylacrylate), poly(methacrylic acid-co-methylmethacrylate) and combinations thereof, preferably poly(methacrylic acid-co-methylmethacrylate) 50:50, poly(methacrylic acid-co-methylmeth-acrylate) 30:70, poly(methacrylic acid-co-dimethylaminoethyl-methacrylate-co-ethylacrylate), poly(methacrylic acid-co-methyl-methacrylate-co-ethylacrylate), and combinations thereof, more preferably poly(methacrylic acid-co-methylmethacrylate) 50:50 having an average molecular weight of about 135,000 g/mol, poly(methacrylic acid-co-methylmethacrylate) 30:70 having an average molecular weight of about 135,000 g/mol, poly(methacrylic acid-co-dimethylaminoethylmethacrylate-co-ethylacrylate) having an average molecular weight of about 750,000 g/mol, poly(methacrylic acid-co-methylmethacrylate-co-ethylacrylate) having an average molecular weight of about 1,000,000 g/mol and combinations thereof.

Other suitable enteric coating materials include: (a) keratin, keratin sandarac-tolu, salol (phenyl salicylate), salol beta-naphthylbenzoate and acetotannin, salol with balsam of Peru, salol with tolu, salol with gum mastic, salol and stearic acid, and salol and shellac; (b) formalized protein, formalized gelatin, and formalized crosslinked gelatin and ion exchange resins; (c) myristic acid-hydrogenated castor oil-cholesterol, stearic acid-mutton tallow, stearic acid-balsam of tolu, and stearic acid-castor oil; (d) shellac, ammoniated shellac, ammoniated shellac-salol, shellac-wool fat, shellac-cetyl alcohol, shellac-stearic acid-balsam of tolu, and shellac n-butyl stearate; (e) abietic acid, methyl abictate, benzoin, balsam of tolu, sandarac, mastic with tolu, and mastic with cetyl alcohol.

The presence and nature of an enteric coating can be chosen according to the desired site of release of the active agent. If the active agent is to be released in the stomach, the particles will usually not comprise an enteric coating layer.

If the active agent is to be released in the duodenum, the enteric coating material is preferably chosen to dissolve at a pH in the range of about 5.0-6.0 and in particular about 5.5-6.0. Particles comprising such an enteric coating are particularly preferred when the active agent is levodopa. Suitable enteric coating materials include poly(methacrylic acid-co-ethyl acrylate) and particularly poly(methacrylic acid-co-ethyl acrylate) 1:1.

If the active agent is to be released in the ileum, the enteric coating material is preferably chosen to dissolve at a pH in the range of about 6.0 to 7.0 and in particular about 6.0 to 6.5. Suitable enteric coating materials include poly(methacrylic acid-co-methyl methacrylate) and particularly poly(methacrylic acid-co-methyl methacrylate) 1:1.

If the active agent is to be released in the colon, the enteric coating material is preferably chosen to dissolve at a pH in the range of about 6.5 to 7.5 and in particular above 7.0. Suitable enteric coating materials include poly(methacrylic acid-co-methyl methacrylate) and poly(methyl acrylate-co-methyl methacrylate-co-methacrylic acid) and particularly poly(methacrylic acid-co-methyl methacrylate) 1:2 and poly(methyl acrylate-co-methyl methacrylate-co-methacrylic acid) 7:3:1.

It is further preferred that the enteric coating layer is present in an amount of 1 to 80 wt. %, particularly 10 to 60 wt. %, and more preferably 30 to 50 wt. %, based on the total weight of the coated particles.

It has surprisingly been found that the oral pharmaceutical composition according to the invention provides a reproducible, site specific and controlled release of active agents whereby the active agents are released initially fast, to have a fast onset of action, and then slowly and substantially continuously over an extended period of time, e.g. over a 1 to 10-hour period, to provide blood levels that are within the therapeutic window. These superior properties reduce the required total daily dose as well as the number of daily doses, thereby reducing both short and long-term side effects.

Without wishing to be bound by any particular theory, it is believed that the bioadhesive material provides for the retention of the multitude of coated particles via adherence to a biological surface at the desired site of absorption of the active agent, such as a desired site within a patient's gastrointestinal tract. The rate of release of the active agent from its complex with the ion exchange resin depends in particular on the ionic strength of the surrounding fluid at the particular site of absorption, which is relatively constant intra and inter patient. An uncontrolled and irregular release of active agent, for instance throughout the patient's gastrointestinal tract, is thus prevented.

The composition preferably exhibits a release of active agent characterized in that the total amount of active agent released is not more than 60 wt. % after 2 h, not more than 70 wt. % after 4 h and not more than 90 wt. % after 8 h (USP method #2, paddle rotation speed 50 rpm, 37° C., dissolution medium 0-1 h: 500 ml 0.1 N HCl, 1-12 h: buffer mixture [500 ml 0.1 N HCl+500 ml phosphate buffer], pH 6.25, ionic strength 0.075).

It is particularly preferred that the composition exhibits a zero order, pseudo-zero order, first order or pseudo-first order release profile. A "zero order" release profile characterizes the release profile of a dosage form that releases a constant amount of drug per unit time. A "pseudo zero order" release profile is one that approximates a zero-order release profile. A "first order" release profile characterizes the release profile of a dosage form that releases a constant percentage of an initial drug charge per unit time. A "pseudo-first order" release profile is one that approximates a first order release profile.

The average particle size of the coated particles is preferably about 20 to about 5000 µm, particularly about 50 to about 4000 µm, and most preferably about 70 to about 3000 µm. It is further preferred that at least about 85%, particularly at least about 95%, and most preferably at least about 98% by volume of the particles have an average particle size within these preferred ranges.

The coated particles typically have a specific gravity (SG) that is higher than the specific gravity of duodenal fluids (SG=1.008–1.03) or intestinal fluids (SG=1.007–1.009). As used herein, the term "specific gravity" means the ratio of the density of the particles to the density of water at 4° C. Preferably the coated particles have a specific gravity in the range from 1.1 to 2.0, more preferably from 1.2 to 1.8. Specific gravity of the coated particles can be calculated from the volume of water displacement ($\Delta V$) resulting from addition of a sample into water at 4° C., the mass of the sample (m) and the density of water at 4° C. ($\rho H_2O$) in accordance with the following formula:

$$SG=(m/\Delta V)/\rho H_2O.$$

The coated particles in accordance with the invention typically exhibit a large specific surface area. As used herein, the term "specific surface area" typically means BET surface area. BET-surface areas can be determined by calculation from desorption data of nitrogen obtained on a BET FlowSorb II 2300 (Micromeritics Instrument Corp., USA) using a mixture of 30 vol. % nitrogen and 70 vol. % helium at 77 K. Preferably, the coated particles exhibit a specific surface area in the range of from about 3,000 to 20,000 $m^2/m^3$. In another embodiment, the coated particles exhibit a specific surface area in the range of from about 1 to 200 $m^2/g$.

In one embodiment, the oral pharmaceutical composition according to the invention comprises coated particles of a complex of at least one active agent with an ion-exchange resin, wherein (i) said particles are coated with a bioadhesive coating layer comprising at least one bioadhesive material and (ii) the coated particles further comprise an enteric coating layer which is placed, preferably directly, over the bioadhesive layer and comprises at least one enteric coating material.

In another embodiment, the oral pharmaceutical composition according to the invention comprises coated particles of a complex of at least one active agent with an ion-exchange resin, wherein (i) said particles are coated with a bioadhesive coating layer comprising at least one bioadhesive material and (ii) at least a portion of the coated particles further comprises a release modifying coating layer which is placed between the complex and the bioadhesive layer and comprises at least one release modifying material.

According to a preferred embodiment, the oral pharmaceutical composition according to the invention comprises coated particles of a complex of at least one active agent with an ion-exchange resin, wherein (i) said particles are coated with a bioadhesive coating layer comprising at least one bioadhesive material and (ii) the coated particles further comprise an enteric coating layer which is placed over the bioadhesive layer and comprises at least one enteric coating material and (iii) at least a portion of the coated particles further comprises a release modifying coating layer which is placed between the complex and the bioadhesive layer and comprises at least one release modifying material.

According to a particularly preferred embodiment, the coated particles comprise:
(a) 1 to 50 wt. %, particularly 5 to 40 wt. % and preferably 10 to 20 wt. % of the at least one active agent;
(b) 1 to 50 wt. %, particularly 10 to 35 wt. % and preferably 15 to 25 wt. % of the ion-exchange resin;
(c) 0 to 50 wt. %, particularly 1 to 50 wt. %, preferably 10 to 40 wt. % and more preferably 15 to 30 wt. % of the release modifying material;
(d) 0.5 to 30 wt. %, particularly 1 to 10 wt. % and preferably 2 to 8 wt. % of the bioadhesive material; and
(e) 0 to 80 wt. %, particularly 1 to 80 wt. %, preferably 10 to 60 wt. % and more preferably 30 to 50 wt. % of the enteric coating material;
based on the total weight of the coated particles.

The composition can further comprise at least one active agent, or a pharmaceutically acceptable salt or solvate thereof, outside the coated particles to provide an immediate boost of active agent. The active agent(s) can be identical with or different from the active agent(s) contained in the coated particles. The active agent(s) can optionally be combined or coated with an enteric material.

The composition according to the invention is particularly suitable for active agents having narrow therapeutic windows such as levodopa, carbidopa, benserazide and/or entacapone.

In a particularly preferred embodiment, the composition comprises levodopa and carbidopa or benserazide in a ratio of 20:1 to 1:1, preferably 15:1 to 2:1, and most preferably 10:1 to 4:1.

In the final formulation, besides the coated particles in the various forms defined above, other suitable substances can be admixed. These other substances can be bound to the ion exchange resin, and coated with some or all of the coating layers defined above as necessary to provide desirable dissolution profile, or they can be in their free native solid or liquid form.

The composition of the invention can further comprise excipients. Suitable types of excipients include adsorbents, antioxidants, acidifying agent, alkalizing agent, buffering agents, colorants, flavorants, sweetening agents, antiadherents, binders, diluents, direct compression excipients, disintegrants, glidants, lubricants, opacifiers and/or polishing agents.

The term "antioxidant" generally refers to an excipient used to inhibit oxidation and thus prevent deterioration of active agents by oxidative processes. Suitable antioxidants include ascorbic acid, ascorbyl palmitate, butylated hydroxyanisole, butylated hydroxytoluene, hypophosphorous acid, monothio-glycerol, propyl gallate, sodium ascorbate, sodium bisulfite, sodium formaldehyde sulfoxylate and sodium metabisulfite.

The term "sweetening agent" generally refers to an excipient used to impart sweetness to a pharmaceutical composition. Suitable sweetening agents include aspartame, dextrose, glycerin, mannitol, saccharin sodium, sorbitol and sucrose.

The term "colorant" generally refers to an excipient used to impart color to a pharmaceutical composition. Suitable colorants include FD&C Red No. 3, FD&C Red No. 20, FD&C Yellow No. 6, FD&C Blue No. 2, D&C Green No. 5, D&C Orange No. 5, D&C Red No. 8, other F.D. & C. dyes, caramel, red ferric oxide, and natural coloring agents such as grape skin extract, beet red powder, beta-carotene, annatto, carmine, turmeric or paprika. The amount of colorant used will vary as desired.

The term "flavorant" generally refers to an excipient used to impart a pleasant flavor and often also odor to a pharmaceutical composition. Suitable flavorants generally include synthetic flavoring oils, flavoring aromatics, natural oils, extracts from whole plants or parts thereof such as leaves, flowers, fruits or combinations thereof. Examples include cinnamon oil, wintergreen oil, peppermint oils, clove oil, bay oil, anise oil, eucalyptus oil, thyme oil, cedar leave oil, nutmeg oil, sage oil, bitter almond oil and cassia oil. Other useful flavorants include vanilla, citrus fruit oils such as lemon, orange, grape, lime or grapefruit oil, and fruit essences such as apple, pear, peach, strawberry, raspberry, cherry, plum, pineapple or apricot essence. Flavorants that have been found to be particularly useful include commercially available orange, grape, cherry and bubble gum flavors and mixtures thereof. The amount of flavoring can depend on a number of factors, including the organoleptic effect desired, can be adapted as needed by those of ordinary skill in the art. Particularly preferred flavors are grape and cherry flavors and citrus fruit flavors such as orange flavor.

Plasticizers can also be included in the pharmaceutical composition to modify the properties and characteristics of the polymers used in the coating layers or core of the composition. The term "plasticizer" generally refers to a compound used to plasticize or soften a component, such as a polymer or binder, of the pharmaceutical composition. Suitable plasticizers generally include low molecular weight polymers, oligomers, copolymers, oils, small organic molecules, low molecular weight polyols having aliphatic hydroxyl groups, ester-type plasticizers, glycol ethers, polypropyleneglycols, multi-block polymers, single-block polymers, low molecular weight polyethyleneglycol, citrate ester-type plasticizers, triacetin, propylene glycol and glycerin. Such plasticizers can also preferably include ethylene glycol, 1,2-butylene glycol, 2,3-butylene glycol, styrene glycol, diethylene glycol, triethylene glycol, tetraethylene glycol and other polyethyleneglycol compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, acetyltributylcitrate, most preferably triethyl citrate, dibutylsebacate, acetyl triethyl citrate, tributyl citrate and allyl glycolate. All such plasticizers are generally commercially available. It is also contemplated that a combination of plasticizers can be used in the present formulation. The PEG based plasticizers are available commercially or can be made by a variety of methods, such as disclosed in "Poly(ethylene glycol) Chemistry: Biotechnical and Biomedical Applications" (J. M. Harris, Ed.; Plenum Press, NY).

The compositions of the invention can also include oils, for example fixed oils, such as peanut oil, sesame oil, cottonseed oil, corn oil and most preferably olive oil, fatty acids such as oleic acid, stearic acid and isostearic acid, fatty acid esters such as ethyl oleate, isopropyl myristate, fatty acid glycerides and acetylated fatty acid glycerides. Optional further ingredients include alcohols such as ethanol, isopropanol, hexadecanol, glycerol and propylene glycol, glycerol ketals such as 2,2-dimethyl-1,3-dioxolane-4-methanol, ethers such as poly(ethyleneglycol) 450, petroleum hydrocarbons such as mineral oil and petrolatum, water or mixtures thereof with or without the addition of a pharmaceutically suitable surfactant, suspending agent or emulsifying agent.

Soaps and synthetic detergents can be employed as surfactants and as vehicles for detergent compositions. Suitable soaps include alkaline, ammonium and triethanolamine salts of fatty acids. Suitable detergents include cationic detergents, such as dimethyl dialkyl ammonium halides, alkyl pyridinium halides and alkylamine acetates, anionic detergents, such as alkyl, aryl and olefin sulfonates, alkyl, olefin, ether and mono-glyceride sulfates and sulfosuccinates. Preferred detergents include amphoteric detergents, such as alkyl-beta-amino-propionates and 2-alkylimidazoline quaternary ammonium salts and mixtures thereof, most preferably nonionic detergents, such as fatty amine oxides, fatty acid alkanolamides and poly(oxyethylene)-block-poly(oxypropylene) copolymers.

Various other components can be added to the compoistion for optimization of a desired active agent release profile including glycerylmonostearate, nylon, cellulose acetate butyrate, d,l-poly(lactic acid), 1,6-hexanediamine, diethylenetriamine, starches, derivatized starches, acetylated monoglycerides, gelatin coacervates, poly(styrene-co-maleic acid), glycowax, castor wax, stearyl alcohol, glycerol palmitostearate, polyethylene, polyvinylacetate, polyvinylchloride, 1,3-butylene-glycoldimethacrylate, ethyleneglycol-dimethacrylate and methacrylate hydrogels.

It should be understood that compounds used in the art of pharmaceutical formulation may serve a variety of functions or purposes. Thus, if a compound named herein is mentioned only once or is used to define more than one term herein, its purpose or function should not be construed as being limited solely to that named purpose(s) or function(s).

The pharmaceutical composition of the invention can assume any shape or form known in the art of pharmaceutical sciences. In particular, it can be a bar, plate, paraboloid of revolution, ellipsoid of revolution or the like. Preferably the composition is in the form of a capsule, such as a hard or soft gelatine or vegetable capsule, a tablet, an oblong tablet, a caplet, a pill, a sphere, a powder or a liquid suspension such as an unhydrous suspension with olive oil, glycerine, polyethylene glycol or other suitable non-ionic vehicle. Most preferably the composition is in the form of a capsule. The final form of the composition can also include surface markings, cuttings, grooves, letters and/or numerals for the purposes of decoration, identification and/or other purposes. The dosage form can include a finish coat to provide the desired shine, color, taste or other aesthetic characteristics. Materials suitable for preparing the finish coat are generally known in the art.

Further preferred embodiments of the composition according to the invention are represented by oral formulations, particularly hard vegetable capsules, comprising:

1) Levodopa/carbidopa in a weight ratio of 4:1, particularly levodopa 50 mg/carbidopa 12.5 mg, wherein carbidopa is in native powder immediate release form, and levodopa is in the form of ion exchange resin/drug particles coated with bioadhesive and enteric coating layers.

2) Levodopa/carbidopa in a weight ratio of 4:1, particularly levodopa 100 mg/carbidopa 25 mg, wherein carbidopa is in native powder immediate release form, and levodopa is in the form of a mixture of ion exchange resin/drug particles coated with bioadhesive and enteric coating layers and ion exchange resin/drug particles coated with release control, bioadhesive and enteric coating layers.

3) Levodopa/carbidopa in a weight ratio of 4:1, particularly levodopa 200 mg/carbidopa 50 mg, wherein carbidopa is in native powder immediate release form, and levodopa is in the form of a mixture of ion exchange resin/drug particles coated with bioadhesive and enteric coating layers and ion exchange resin/drug particles coated with release control, bioadhesive and enteric coating layers.

4) Levodopa/entacapone/carbidopa in a weight ratio of 5-25:20:1-5, particularly levodopa 50-250 mg, entacapone 200 mg, carbidopa 10-50 mg, wherein levodopa is in the form of a mixture of ion exchange resin/drug particles coated with bioadhesive and enteric coating layers and ion exchange resin/drug particles coated with release control, bioadhesive and enteric coating layers, and entacapone and carbidopa are in form of ion exchange resin/drug particles coated with bioadhesive and enteric coating layers or in native powder forms.

Alternatively, in the above embodiments, carbidopa can be replaced by benserazide.

The oral pharmaceutical composition of the present invention can be prepared by methods generally known in the art. A typical process for preparing the composition comprises the steps of:

(i) contacting an active agent with an ion-exchange resin to obtain an active agent/ion exchange resin complex;
(ii) optionally coating the complex of step (i) with a coating layer comprising a release modifying material;
(iii) coating the complex of step (i) or the coated complex of step (ii) with a coating layer comprising a bioadhesive material; and
(iv) optionally coating the coated complex of step (iii) with a coating layer comprising an enteric coating material.

In step (i), the active agent is preferably mixed with an aqueous suspension of the resin, and the resulting complex is washed and dried. Adsorption of active agent onto the resin can be detected by measuring a change in the pH of the reaction medium, or by measuring a change in concentration of counterions and/or active agent. The complex is typically washed with an alcohol such as ethanol and/or water to insure removal of any unbound active agent. The complexes are usually air-dried in trays at room temperature or elevated temperature. The binding can be performed, for example, as a batch or column process, as is known in the art.

Binding of active agent to resin can generally follow one of four general reaction types. In the case of binding a basic active agent to a cation exchange resin these are: (a) resin (salt form, e.g. $Na^+$-form) plus active agent (salt form), (b) resin (salt form, e.g. $Na^+$-form) plus active agent (free base), (c) resin ($H^+$-form) plus active agent (salt form), and (d) resin ($H^+$-form) plus active agent (free base). In the case of binding an acidic active agent to an anion exchange resin these are: (a) resin (salt form, e.g. $Cl^-$-form) plus active agent (salt form), (b) resin (salt form, e.g. $Cl^-$-form) plus active agent (free acid), (c) resin ($OH^-$-form) plus active agent (salt form); and (d) resin ($OH^-$-form) plus active agent (free acid). All of these reactions except (d) involve by-products formed by a competition of counterions with the active agent for binding sites on the resin, thereby reducing the amount of active agent bound at equilibrium. Thus, both for acidic and basic active agent truly stoichiometric binding of active agent to resin is accomplished only through reaction (d).

In steps (ii) to (iv), conventional coating solvents and coating procedures, such as fluid bed coating or spray coating, can be employed to coat the particles. Techniques of fluid bed coating are taught, for example, in U.S. Pat. Nos. 3,089,824, 3,117,027 and 3,253,944. The coating is normally applied to the complex of active agent and ion exchange resin, but alternatively can be applied to the resin before complexing with the active agent. The coating mixture is typically applied as a solution, dispersion or emulsion in a coating solvent. Examples of suitable coating solvents include methanol, ethanol, isopropanol, isobutanol, n-butyl acetate, ethyl acetate, acetone, methyl ethyl ketone, hexane, methyl isobutyl ketone, carbon tetrachloride, methylene chloride, ethylene chloride, trichloroethylene, tetrahydrofuran, 2-nitropropane, toluene, xylene, mixtures thereof such as a mixture of methylene chloride and acetone. Methanol, ethanol, isopropanol, isobutanol, n-butyl acetate and ethyl acetate are preferred.

The invention will be further illustrated by way of the following examples.

EXAMPLES

Release of levodopa was measured spectrophotometrically at 280 nm.

Example 1

A) Preparation of Levodopa Drug Resin Complex (LDRC)

400 g of a sodium polystyrene sulfonate cation exchange resin crosslinked with divinylbenzene (125-400 mesh) were mixed with 1200 ml of deionized water under slow stirring for 1 h. The resin was allowed to settle and the water was decanted. Diluted HCl was prepared by adding 300 ml of conc. HCl to 1200 ml of deionized water and mixing. The resin was mixed with 250 ml of the diluted HCl for 30 min and then allowed to settle, the supernatant was decanted and this step was repeated until all of the diluted HCl had been used up. The resin was washed by mixing with 500 ml of deionized water for min, allowing the resin to settle, decanting the super-natant and repeating this step 8 times or until the supernatant was neutral to litmus paper.

A mixture of 300 ml of ethanol and 300 ml of deionized water was added to the resin and 250 g of levodopa were added and treated with the resin for 4 h while mixing for 1 min every 30 min. The resin was allowed to settle overnight and then the supernatant was decanted. The resin was washed by mixing with 300 ml of a water/ethanol (3:2) mixture, allowing the resin to settle, decanting the supernatant and repeating this step until no levodopa crystals were visible under a microscope after evaporating the supernatant. The obtained levodopa drug resin complex was dried in a furnace at 60° C. Moisture content (LOD [loss on drying]): 5±0.5 wt. %, levodopa content (HPLC): 40±1 wt. %. The obtained complex was found to be stable against exposure to air at room temperature for at least 6 months.

Figure 1:
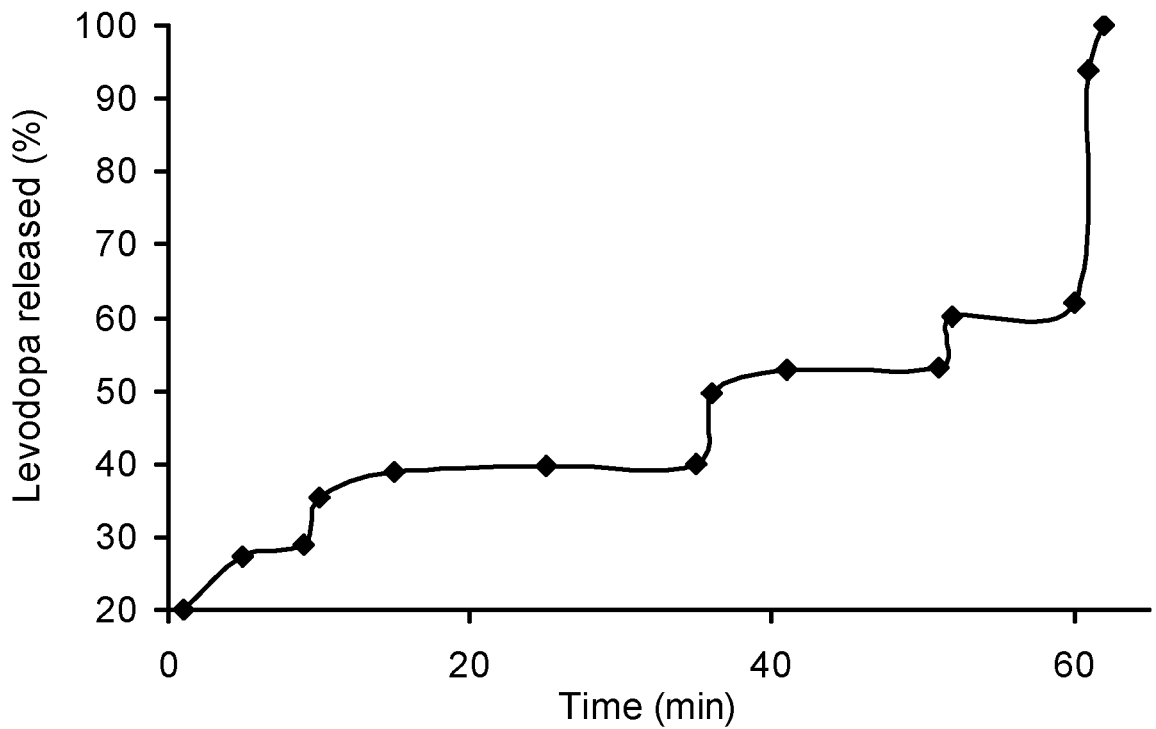
FIG. 1 shows the release of levodopa from 500 mg of the levodopa drug resin complex obtained in Example 1A dispersed in deionized water at room temperature under stirring with a magnetic stirrer. NaCl was added as follows: 9 min: 200 mg; 36 min: 700 mg; 52 min: 1200 mg; 61 min: 3300 mg.

Ionic binding of levodopa in the complex was tested by adding increasing amounts of electrolyte (NaCl) to a slurry of LDRC in deionized water. Release of levodopa is shown in FIG. 1.

B) Coating with a Release Modifying Coating Layer

|  | Example | | | |
| --- | --- | --- | --- | --- |
|  | 1B-1 | 1B-2 | 1B-3 | 1B-4 |
| Release modifying material | 20% | 30% | 40% | 50% |
| Drug resin complex (Example) | 1A | 1A | 1A | 1A |
| Drug resin complex (g) | 74 | 58 | 58 | 58 |
| Coating dispersion |  |  |  |  |
| Ethylcellulose (g) | 20 |  |  |  |
| Ethylcellulose (g) |  | 124 | 212 | 290 |

-continued

| | Example | | | |
|---|---|---|---|---|
| | 1B-1 | 1B-2 | 1B-3 | 1B-4 |
| (pre-plasticized, 20 wt % solids) | | | | |
| Dibutyl sebacate (g) | 4 | | | |
| Olive oil (g) | 2 | | | |
| Ethanol 96 vol. % (g) | 374 | | | |
| Deionized water (g) | | 83 | 141 | 193 |
| Coating conditions | | | | |
| Nozzle diameter (mm) | 0.5 | 0.5 | 0.5 | 0.5 |
| Fluidizing air pressure (bar) | 0.2 | 0.2 | 0.2 | 0.2 |
| Fluidizing air temperature (° C.) | 50 | 75 | 75 | 75 |
| Nozzle air pressure (bar) | 2 | 1.5 | 1.5 | 1.5 |
| Product temperature (° C.) | 30 | 37 | 37 | 37 |
| Pump speed (g/min) | 2 | 2.5 | 2.5 | 2.5 |
| Yield (g) | 95 | 80 | 98 | 110 |
| Moisture content (wt. %, LOD) | 5 | 5 | 5 | 5 |
| Levodopa content (wt. %, HPLC) | 29 | 27 | 23 | 20 |

Levodopa drug resin complex (Ldrc) was fluidized and sprayed with coating dispersion using a Mini-Glatt coating apparatus and dried in situ to 45-50° C. The product was sifted through a 40 mesh stainless steel screen. Microscopic examination revealed uniformly coated particles with moderate agglomeration. The coated products obtained in Examples 1B-2 to 1B-4 were further cured for 2 h at 60° C.

Figure 2:
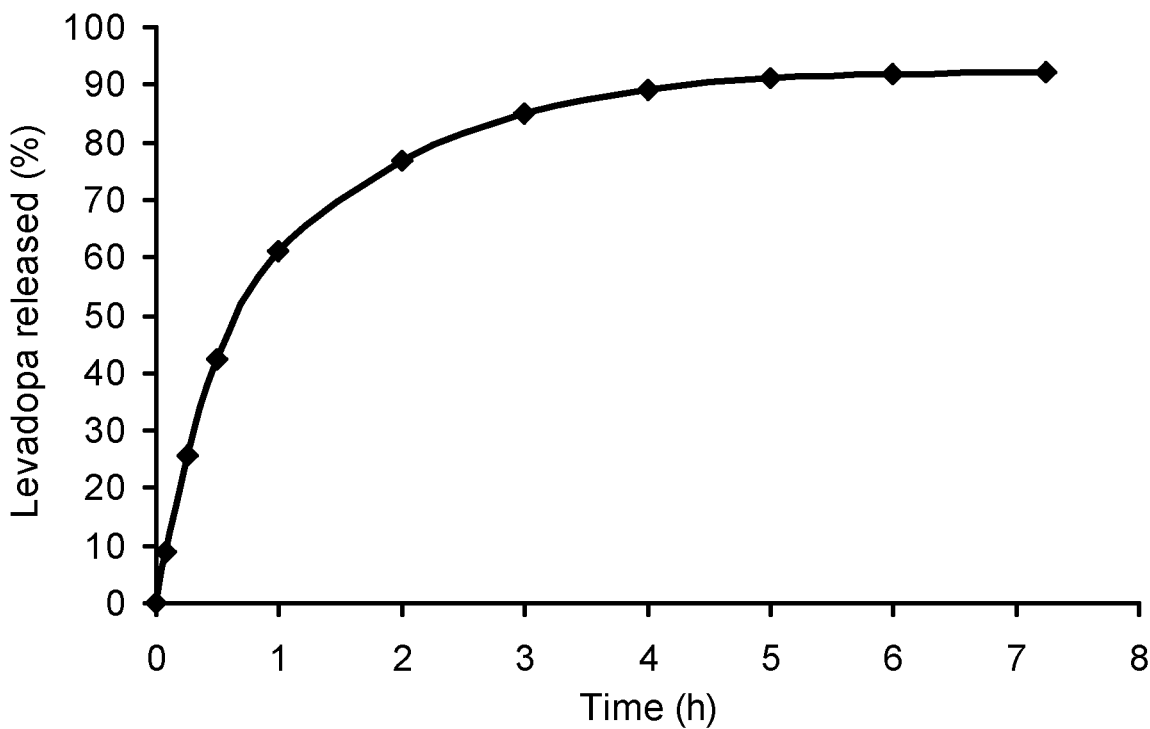
FIG. 2 shows the dissolution profile of coated LDRC obtained in Example 1B-1 in phosphate buffer (USP method #2, paddle rotation speed 50 rpm, 37° C., pH 5.5, ionic strength 0.075).
Figure 3:
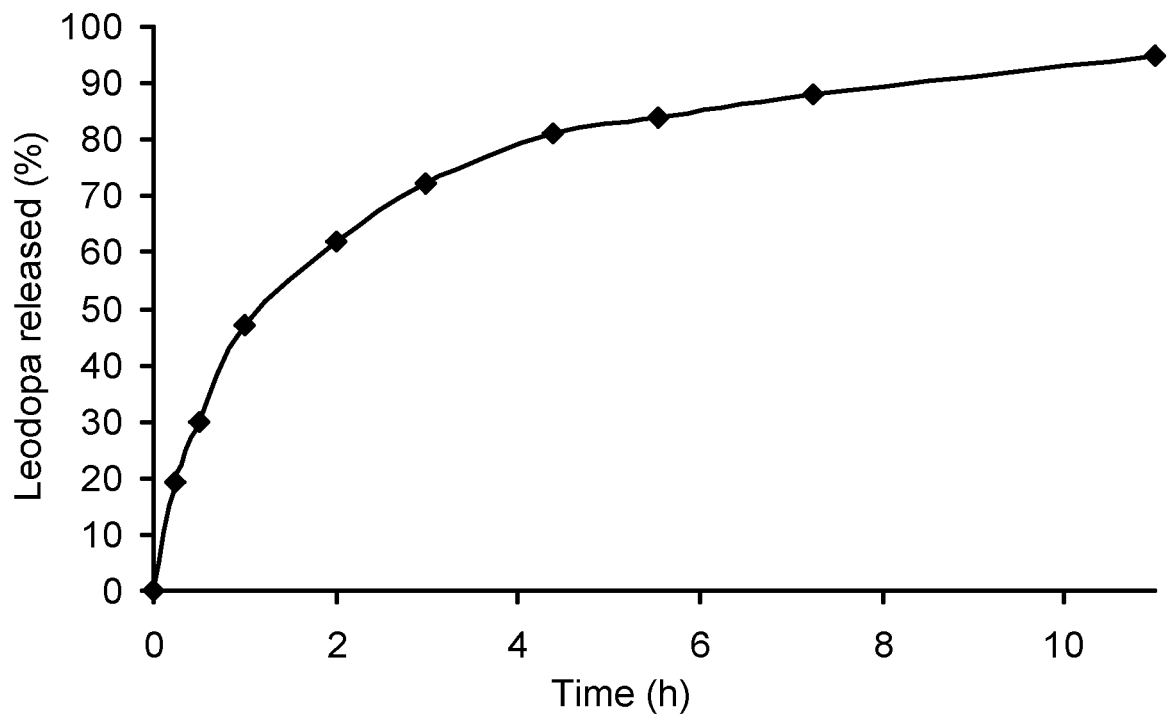
FIG. 3 shows the dissolution profile of coated LDRC obtained in Example 1B-3 in phosphate buffer (USP method #2, paddle rotation speed 50 rpm, 37° C., pH 5.5, ionic strength 0.075)
Figure 4:
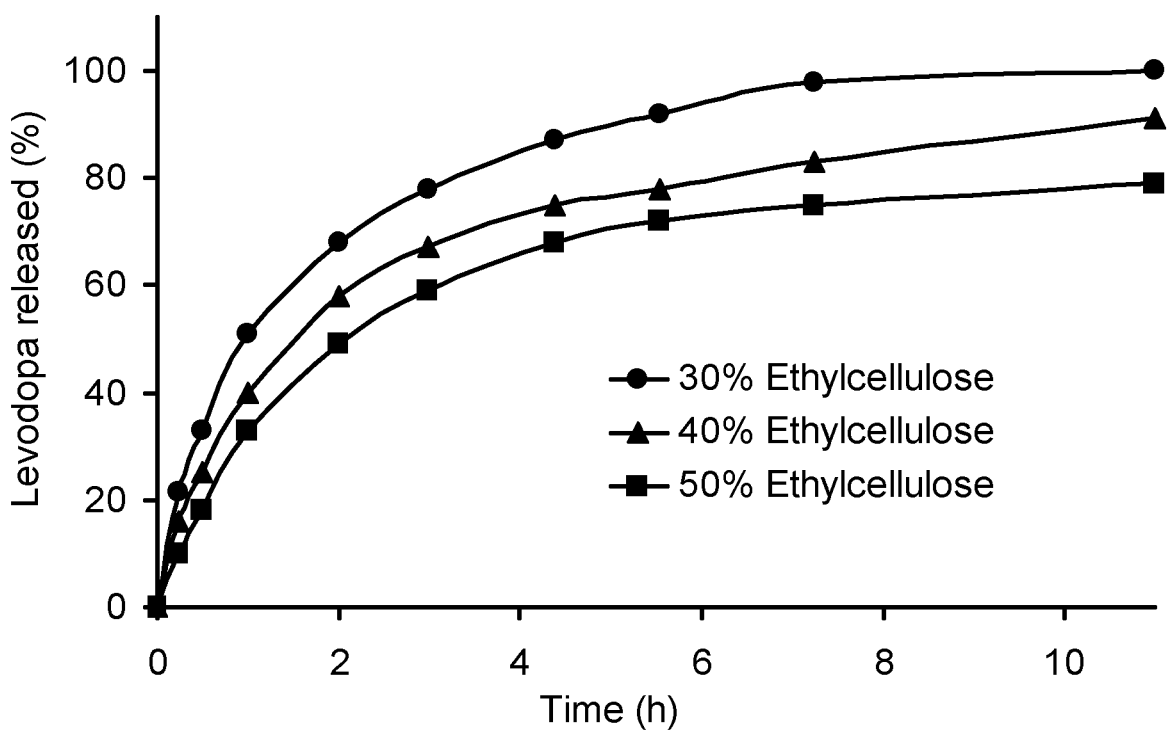
FIG. 4 shows the dissolution profiles of coated LDRC obtained in Examples 1B-2 to 1B-4 in phosphate buffer (USP method #2, paddle rotation speed 50 rpm, 37° C., pH 6.0, ionic strength 0.075).

Dissolution profiles of coated LDRC obtained in Examples 1B-1 and 1B-3 in phosphate buffer (USP method #2, paddle rotation speed 50 rpm, 37° C., pH 5.5, ionic strength 0.075) are shown in FIGS. 2 and 3. Dissolution profiles of coated LDRC obtained in Examples 1B-2 to 1B-4 in phosphate buffer (USP method #2, paddle rotation speed 50 rpm, 37° C., pH 6.0, ionic strength 0.075) are shown in FIG. 4.

C) Coating with a Bioadhesive Coating Layer

| | Example | | | | |
|---|---|---|---|---|---|
| | 1C-1 | 1C-2 | 1C-3 | 1C-4 | 1C-5 |
| Release modifying material | — | 30% | 40% | 50% | 40% |
| Bioadhesive material | 5% | 5% | 5% | 5% | 10% |
| Drug resin complex (Example) | 1A | 1B-2 | 1B-3 | 1B-4 | 1B-3 |
| Drug resin complex (g) | 57 | 57 | 57 | 57 | 54 |
| Coating dispersion | | | | | |
| Carboxypolymethylene* (g) | 3 | 3 | 3 | 3 | 6 |
| Ethanol 96 vol. % (g) | 197 | 197 | 197 | 197 | 194 |
| Coating conditions | | | | | |
| Nozzle diameter (mm) | 0.5 | 0.5 | 0.5 | 0.5 | 0.5 |
| Fluidizing air pressure (bar) | 0.15-0.7 | 0.15-0.7 | 0.15-0.7 | 0.15-0.7 | 0.15-0.7 |
| Fluidizing air temperature (° C.) | 50 | 50 | 50 | 50 | 65 |
| Nozzle air pressure (bar) | 1.5 | 1.5 | 1.5 | 1.5 | 1.5 |
| Product temperature (° C.) | 37 | 37 | 37 | 37 | 35 |
| Pump speed (g/min) | 3 | 3 | 3 | 3 | 2.5 |
| Yield (g) | 59 | 59 | 59 | 59 | 59 |
| Moisture content (wt. %, LOD) | 5.5 | 5.5 | 5.5 | 5.5 | 4.5 |
| Levodopa content (wt. %, HPLC) | 38 | 26 | 21 | 19 | 20 |

*High molecular weight polymer of acrylic acid crosslinked with allyl ethers and pentaerythritol Levodopa drug resin complex (LDRC) was fluidized and sprayed with coating dispersion using a Mini-Glatt coating apparatus and dried in situ to 50° C. The product was sifted through a mesh stainless steel screen. Microscopic examination revealed uniformly coated particles with moderate agglomeration.

Figure 5:
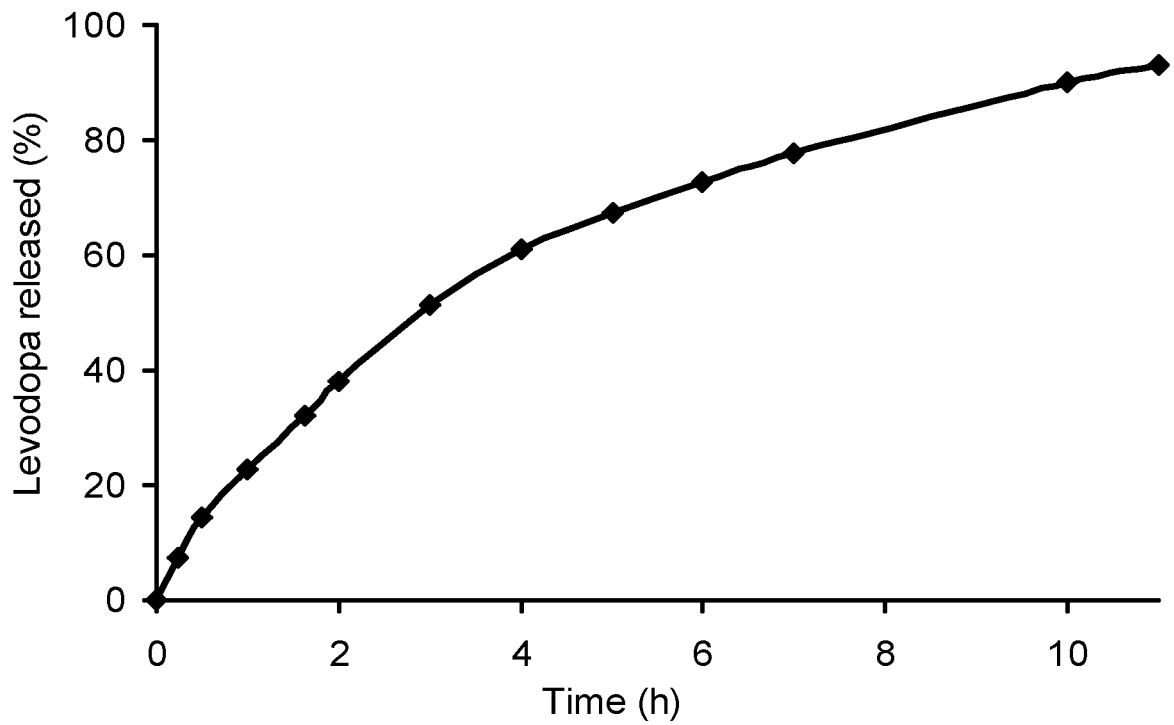
FIG. 5 shows the dissolution profile of coated LDRC obtained in Example 1C-3 in phosphate buffer (USP method #2, paddle rotation speed 50 rpm, 37° C., pH 6.0, ionic strength 0.075).
Figure 6:
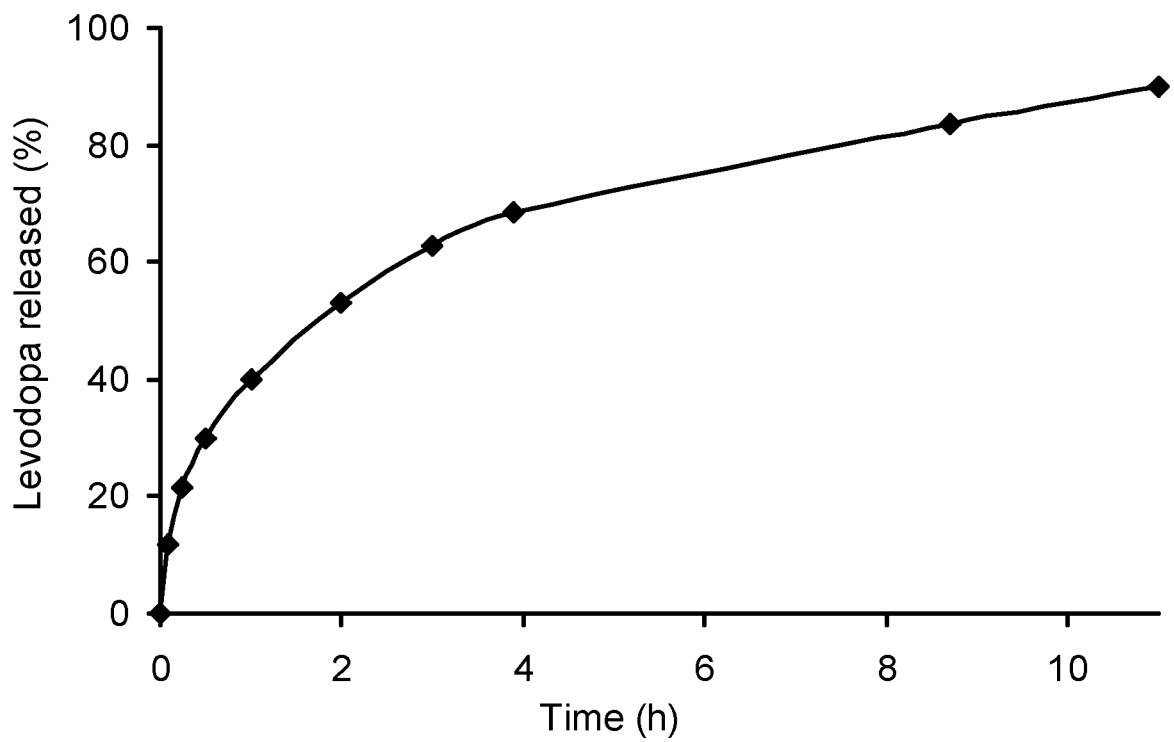
FIG. 6 shows the dissolution profile of coated LDRC obtained in Example 1C-5 in phosphate buffer (USP method #2, paddle rotation speed 50 rpm, 37° C., pH 6.0, ionic strength 0.075).

Dissolution profiles of coated LDRC obtained in Examples 1C-3 and 1C-5 in phosphate buffer (USP method #2, paddle rotation speed 50 rpm, 37° C., pH 6.0, ionic strength 0.075) are shown in FIGS. 5 and 6.

D) Coating with an Enteric Coating Layer

| | Example | | | |
|---|---|---|---|---|
| | 1D-1 | 1D-2 | 1D-3 | 1D-4 |
| Release modifying material | — | 30% | 40% | 50% |
| Bioadhesive material | 5% | 5% | 5% | 5% |
| Amount of enteric coating mat. | 40% | 40% | 40% | 40% |
| Drug resin complex (Example) | 1C-1 | 1C-2 | 1C-3 | 1C-4 |
| Drug resin complex (g) | 58 | 58 | 58 | 58 |
| Coating dispersion | | | | |
| Methacrylic acid copolymer* (g) | 35 | 35 | 35 | 35 |
| Triethyl citrate (g) | 3.5 | 3.5 | 3.5 | 3.5 |
| Ethanol 96 vol. % (g) | 300 | 300 | 300 | 300 |
| Coating conditions | | | | |
| Nozzle diameter (mm) | 0.5 | 0.5 | 0.5 | 0.5 |
| Fluidizing air pressure (bar) | 0.4-0.6 | 0.4-0.6 | 0.4-0.6 | 0.4-0.6 |
| Fluidizing air temperature (° C.) | 60 | 60 | 60 | 60 |
| Nozzle air pressure (bar) | 1.5 | 1.5 | 1.5 | 1.5 |
| Product temperature (° C.) | 45 | 45 | 45 | 45 |
| Pump speed (g/min) | 3 | 3 | 3 | 3 |
| Yield (g) | 95 | 94 | 96 | 95 |
| Moisture content (wt. %, LOD) | 5.1 | 5.3 | 5.0 | 4.9 |
| Levodopa content (wt. %, HPLC) | 23 | 16 | 12 | 11 |

*Commercially available methacrylic acid copolymer with dispersing agents formulated for easy dispersion in water Levodopa drug resin complex (LDRC) was fluidized and sprayed with coating dispersion using a Mini-Glatt coating apparatus and dried in situ to 55° C. The product was sifted through a mesh stainless steel screen. Microscopic examination revealed uniformly coated particles with moderate agglomeration.

Figure 7:
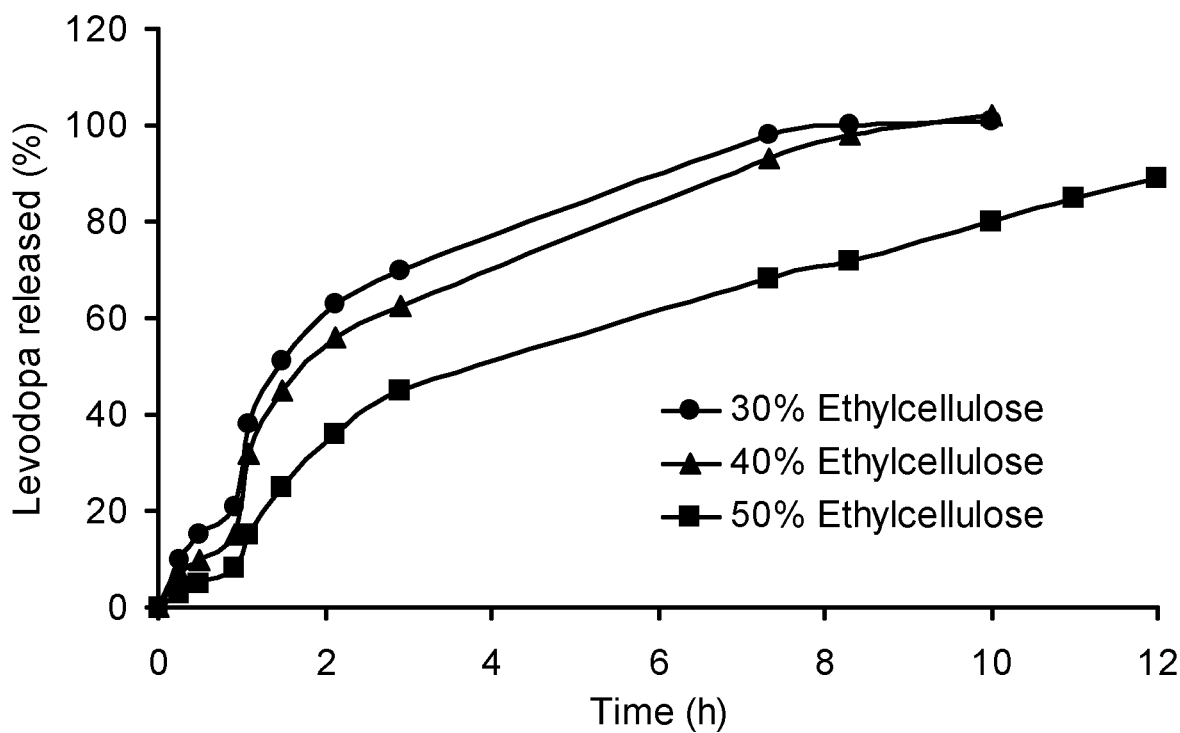
FIG. 7 shows the dissolution profiles of coated LDRC obtained in Examples 1D-2 to 1D-4 in phosphate buffer (USP method #2, paddle rotation speed 50 rpm, 37° C., dissolution medium 0-1 h: 0.1 N HCl, 1-12 h: phosphate buffer pH 6.25, ionic strength 0.075).
Figure 8:
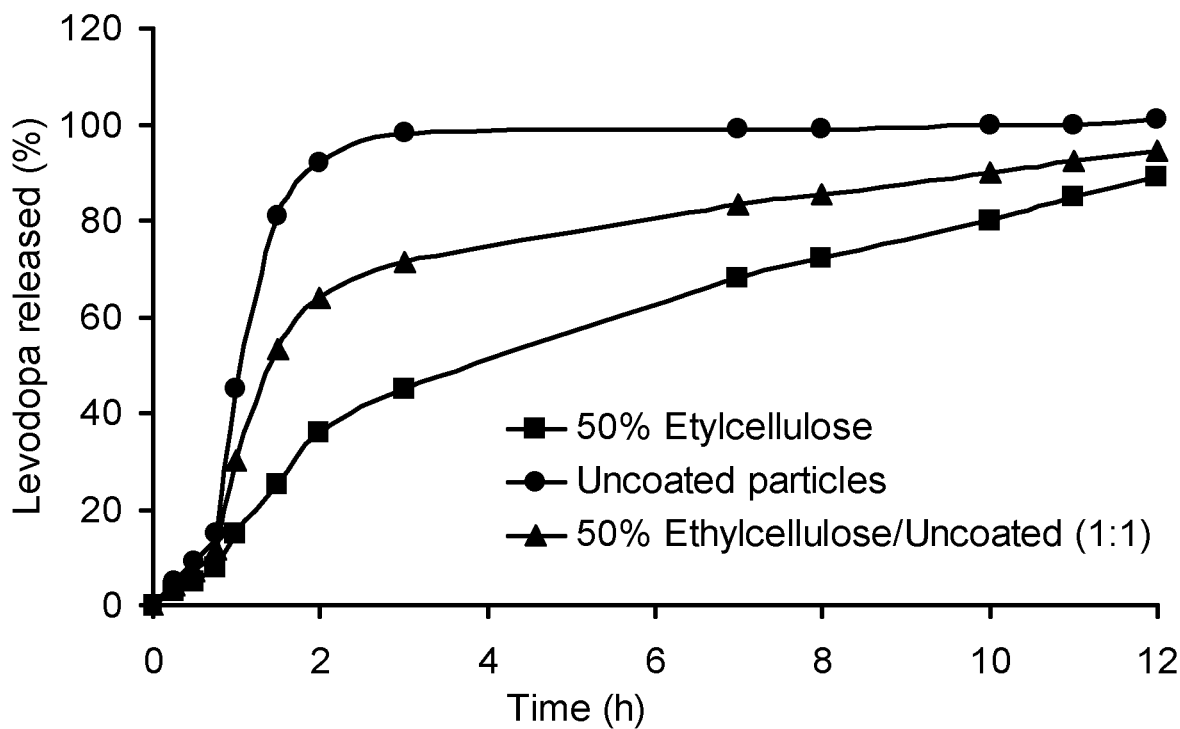
FIG. 8 shows the dissolution profiles of coated LDRC obtained in Examples 1D-1 and 1D-4 in phosphate buffer (USP method #2, paddle rotation speed 50 rpm, 37° C., dissolution medium 0-1 h: 0.1 N HCl, 1-12 h: phosphate buffer pH 6.25, ionic strength 0.075).

Dissolution profiles of coated LDRC obtained in Examples 1D-2 to 1D-4 in phosphate buffer (USP method #2, paddle rotation speed 50 rpm, 37° C., dissolution medium 0-1 h: 0.1 N HCl, 1-12 h: phosphate buffer pH 6.25, ionic strength 0.075) are shown in FIG. 7. Dissolution profiles of coated LDRC obtained in Examples 1D-1 and 1D-4 in phosphate buffer (USP method #2, paddle rotation speed 50 rpm, 37° C., dissolution medium 0-1 h: 0.1 N HCl, 1-12 h: phosphate buffer pH 6.25, ionic strength 0.075) are shown in FIG. 8.

E) Hard Gelatin Capsules Comprising Levodopa and Carbidopa

| | Example | |
|---|---|---|
| | 1E-1 | 1E-2 |
| LDRC from Example 1D-1 (mg) | 218.0 | 130.0 |
| LDRC from Example 1D-4 (mg) | — | 635.0 |
| Carbidopa (mg) | 12.5 | 25.0 |
| Magnesium stearate or talcum (mg) | 10.5 | 20.0 |

|  | Example | |
|---|---|---|
|  | 1E-1 | 1E-2 |
| Total (mg) | 241.0 | 810.0 |
| Levodopa content (mg) | 50.0 | 100.0 |
| Carbidopa content (mg) | 12.5 | 25.0 |

One or more levodopa drug resin complexes were dry mixed with carbidopa and magnesium stearate or talcum as indicated. The obtained mixture was filled into hard gelatin capsules.

F) Tablet Comprising Levodopa and Carbidopa

|  | Example 1F |
|---|---|
| LDRC from Example 1D-4 (mg) | 909 |
| Carbidopa (mg) | 25 |
| Sodium carboxymethylcellulose (mg) | 50 |
| Maize starch (mg) | 25 |
| Talc (mg) | 25 |
| Magnesium stearate (mg) | 41 |
| Total (mg) | 1075 |
| Levodopa content (mg) | 100 |
| Carbidopa content (mg) | 25 |
| Tablet diameter (mm) | 10 |
| Hardness (kg/cm$^2$) | 5 |

Levodopa drug resin complex was dry mixed with carbidopa and excipients as indicated. The obtained mixture was compressed into tablets.

Examples 2-5

A) Preparation of Drug Resin Complexes (DRCS)

2A) Preparation of Ropinirole Drug Resin Complex (RoDRC)

100 g of sodium polystyrene sulfonate cation exchange resin crosslinked with divinylbenzene (125-400 mesh) was added to 500 ml of deionized deaerated water and mixed occasionally under argon for 1 h. The resulting slurry was transferred to a 250 ml glass column and washed with 200 ml of deionized deaerated water. 40 g of ropinirole hydrochloride was dissolved in 300 ml deionized deaerated water and passed through the column at a rate of 10 ml per min. The column was washed with 1000 ml of deionized deaerated water. The obtained drug resin complex was taken out of the column and dried first on filter paper and then in vacuum over silica to a moisture content of 5 wt. %.

Figure 9:
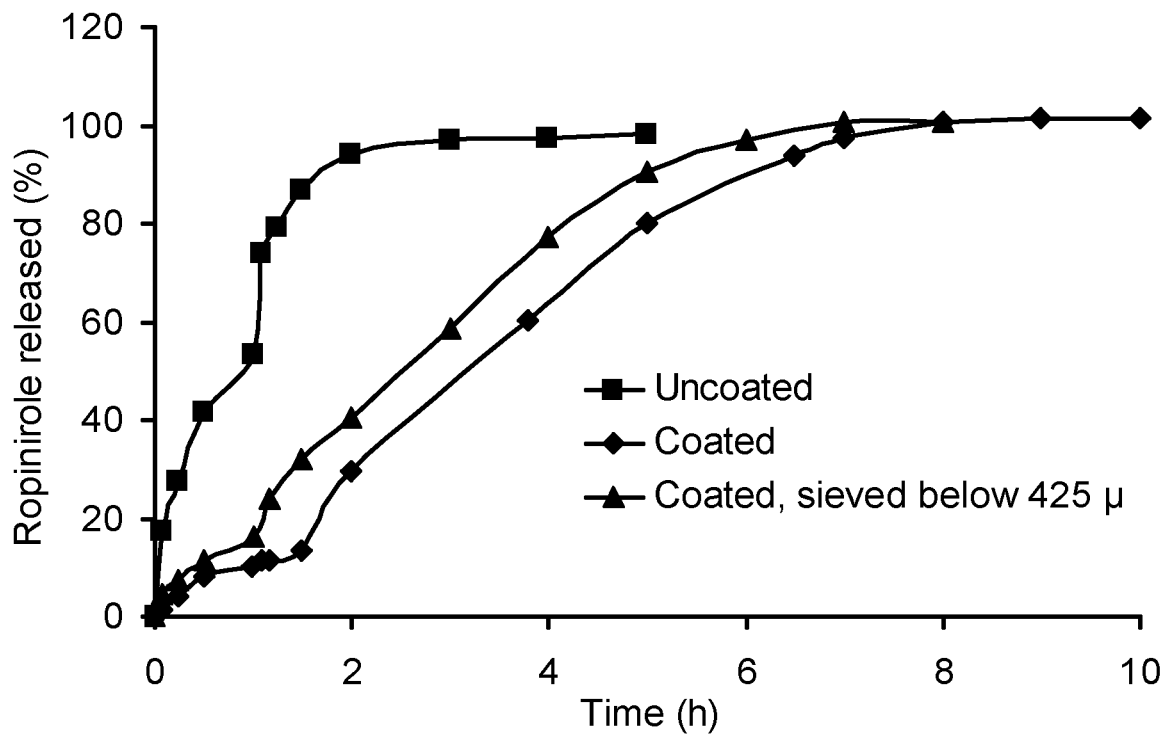
FIG. 9 shows the dissolution profiles of uncoated ropinirole drug resin complex (RoDRC) obtained in Example 2A and coated RoDRC obtained in Example 2D before and after sieving (USP method #2, paddle rotation speed 75 rpm, 37° C., dissolution medium 0-1 h: 500 ml 0.1 N HCl, 1-10 h: buffer mixture [500 ml 0.1 N HCl+500 ml phosphate buffer], pH 5.6, ionic strength 0.075).

The dissolution profile of the obtained uncoated ropinirole drug resin complex (RoDRC; USP method #2, paddle rotation speed rpm, 37° C., dissolution medium 0-1 h: 0.1 N HCl, 1-10 h: buffer mixture [500 ml 0.1 N HCl+500 ml phosphate buffer], pH 5.6, ionic strength 0.075) is shown in FIG. 9.

3A) Preparation of Alendronate Drug Resin Complex (AlDRC)

50 g of cholestyramine anion exchange resin (Cl$^-$-form, 99%<100μ, 56%<50μ) was washed with 5×200 ml of deaerated water. The final portion of water was decanted after 5 h. 300 ml of deaerated water and 16.25 g of alendronate sodium were added to the resin. The resulting slurry was mixed at room temperature for 60 min, centrifuged and the solvent decanted. This was repeated three more times until a total of 65 g of alendronate sodium had been used. The obtained drug resin complex was washed with 3 l of water and dried first on filter paper and then in vacuum over silica to a moisture content of 5 wt. %.

4A) Preparation of Risperidone Drug Resin Complex (RiDRC)

100 g of polystyrene sulfonate cation exchange resin crosslinked with divinylbenzene (H$^+$-form) was washed with 500 ml of deionized deaerated water for 30 min. The water was decanted and the resin was washed with 300 ml 96% ethanol. 100 g of risperidone was added to 300 ml of 96% ethanol. The slurry was heated to 60° C., added to the resin and mixed for 12 h under argon. The solvent was decanted and the resin was washed with 5×250 ml of 96% ethanol. The last portion of ethanol was left overnight under argon. The ethanol was decanted and the obtained drug resin complex was dried first on filter paper and then in vacuum over silica to a moisture content of 5 wt. %.

5A) Preparation of Olanzapine Drug Resin Complex (OzDRC)

100 g of polystyrene sulfonate cation exchange resin crosslinked with divinylbenzene (H$^+$-form) was washed with 500 ml of deaerated 96% ethanol. The ethanol was decanted. 80 g of olanzapine was dispersed in 500 ml of deaerated 96% ethanol at 40° C. and added to the resin. The resulting slurry was mixed for 5 h at 40° C. under argon and then left overnight at room temperature. The solvent was decanted and the obtained olanzapine drug resin complex was washed with 10×500 ml of deaerated 96% ethanol. The obtained drug resin complex was dried first on filter paper and then in vacuum over silica to a moisture content of 5 wt. %.

B) Coating with a Release Modifying Coating Layer

2B) Coating RoDRC with a Release Modifying Coating Layer

| Release modifying material | 43% |
|---|---|
| Drug resin complex from 2A (g) | 65 |
| Ethylcellulose (g) (pre-plasticized, 25 wt % solids) | 193 |
| Deionized water (g) | 128 |
| Coating conditions |  |
| Nozzle diameter (mm) | 0.5 |
| Fluidizing air pressure (bar) | 0.25 |
| Fluidizing air temperature (° C.) | 70-75 |
| Nozzle air pressure (bar) | 1.5 |
| Product temperature (° C.) | 25 |
| Pump speed (g/min) | 3 |
| Yield (g) | 95 |
| Moisture content (wt. %, LOD) | 5 |

Ropinirole drug resin complex (RoDRC) was fluidized and sprayed with coating dispersion using a Mini-Glatt coating apparatus analogous to Example 1B.

3B) Coating AlDRC with a Release Modifying Coating Layer 25 g of ethylcellulose was thoroughly mixed with 30 ml of 99% ethanol and 0.5 g glycerin used as a plasticizer. The obtained mixture was added to 40 g of the alendronate drug resin complex prepared in Example 3A and mixed until the mixture was homogeneous. The wet mass was forced through a 425 μ sieve and dried at 60° C. for 2 h. The obtained granulate was sieved through a 425 μ sieve.

C) Coating with a Bioadhesive Coating Layer

|  | Example | | | |
|---|---|---|---|---|
|  | 2C | 3C | 4C | 5C |
| Release modifying material | 39% | 35% | — | — |
| Bioadhesive material | 9% | 9% | 10.6% | 13% |
| Drug resin complex (Example) | 2B | 3B | 4A | 5A |
| Drug resin complex (g) | 100 | 100 | 84 | 67 |
| Coating dispersion | | | | |
| Carboxypolymethylene* (g) | 10 | 10 | 10 | 10 |
| Ethanol 96 vol. % (g) | 90 | 90 | 90 | 120 |
| Water (g) | 4 | 4 | 4 | 4 |
| Coating conditions | | | | |
| Nozzle diameter (mm) | 0.5 | 0.5 | 0.5 | 0.5 |
| Fluidizing air pressure (bar) | 0.22 | 0.22 | 0.2-0.3 | 0.2-0.25 |
| Fluidizing air temperature (° C.) | 60 | 60 | 60 | 60 |
| Nozzle air pressure (bar) | 1.5 | 1.5 | 1.5 | 1.5 |
| Product temperature (° C.) | 38 | 36 | 30-38 | 23-40 |
| Pump speed (g/min) | 1-3 | 3 | 3 | 3 |
| Peristaltic pump hose internal diameter (mm) | 2 | 2 | 2 | 2 |

*High molecular weight polymer of acrylic acid crosslinked with allyl ethers and pentaerythritol Drug resin complexes were fluidized and sprayed with coating dispersion using a Mini-Glatt coating apparatus analogous to Example 1C.

D) Coating with an Enteric Coating Layer

|  | Example | | | |
|---|---|---|---|---|
|  | 2D | 3D | 4D | 5D |
| Release modifying material | 28% | 25% | — | — |
| Bioadhesive material | 6% | 6% | 7% | 9% |
| Amount of enteric coating mat. | 29% | 29% | 31% | 31% |
| Drug resin complex (Example) | 2C | 3C | 4C | 5C |
| Drug resin complex (g) | 100 | 100 | 94 | 77 |
| Coating dispersion | | | | |
| Methacrylic acid copolymer* (g) | 35 | 35 | 35 | 35 |
| Triethyl citrate (g) | 5 | 5 | 5 | 4 |
| Ethanol 96 vol. % (g) | 300 | 300 | 300 | 300 |
| Coating conditions | | | | |
| Nozzle diameter (mm) | 0.5 | 0.5 | 0.5 | 0.5 |
| Fluidizing air pressure (bar) | 0.3-0.4 | 0.2 | 0.3 | 0.3 |
| Fluidizing air temperature (° C.) | 60 | 60 | 60 | 60 |
| Nozzle air pressure (bar) | 1.5 | 1.2 | 1.5 | 1.5 |
| Product temperature (° C.) | 27-42 | 30-48 | 35-37 | 35-37 |
| Pump speed (g/min) | 5 | 5 | 5 | 5 |
| Peristaltic pump hose internal diameter (mm) | 2 | 2 | 2 | 2 |
| Active agent content (wt. %, HPLC) | 9.3 | 22 | 20.3 | 10.8 |

*Commercially available methacrylic acid copolymer with dispersing agents formulated for easy dispersion in water Drug resin complexes were fluidized and sprayed with coating dispersion using a Mini-Glatt coating apparatus analogous to Example 1D.

Dissolution profiles of coated ropinirole drug resin complexes obtained in Example 2D before and after sieving in phosphate buffer (USP method #2, paddle rotation speed 75 rpm, 37° C., dissolution medium 0-1 h: 500 ml 0.1 N HCl, 1-10 h: buffer mixture [500 ml 0.1 N HCl+500 ml phosphate buffer], pH 5.6, ionic strength 0.075) are shown in FIG. 9.

Figure 10:
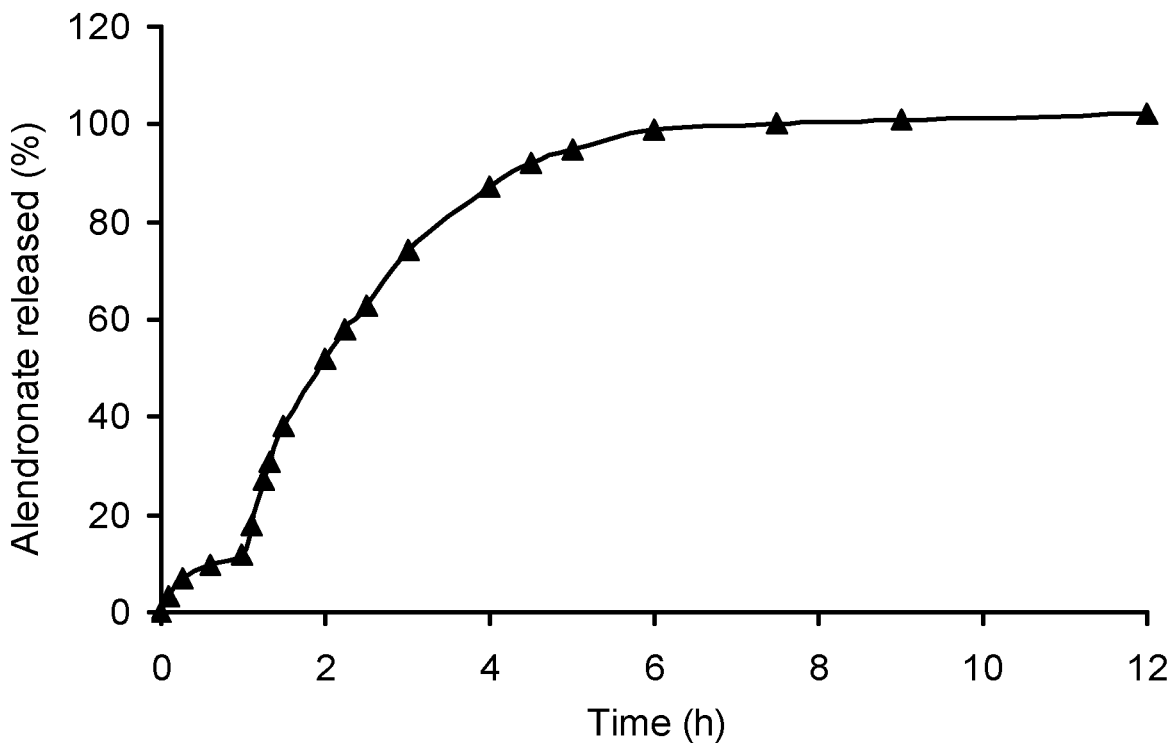
FIG. 10 shows the dissolution profile of coated alendronate drug resin complex (AlDRC) obtained in Example 3D (USP method #2, paddle rotation speed 75 rpm, 37° C., dissolution medium 1000 ml 0.1 M NaCl).
Figure 11:
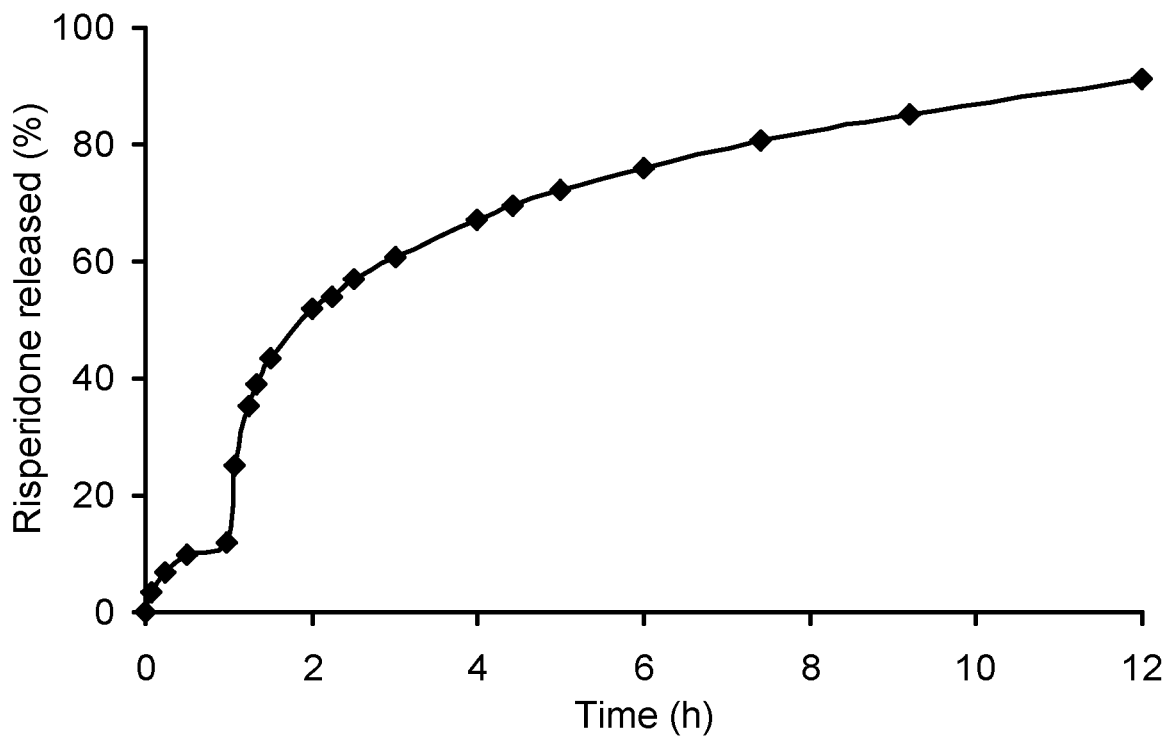
FIG. 11 shows the dissolution profile of coated risperidone drug resin complex (RiDRC) obtained in Example 4D (USP method #2, paddle rotation speed 75 rpm, 37° C., dissolution medium 0-1 h: 500 ml 0.1 N HCl, 1-12 h: buffer mixture [500 ml 0.1 N HCl+500 ml phosphate buffer], pH 5.6, ionic strength 0.075).
Figure 12:
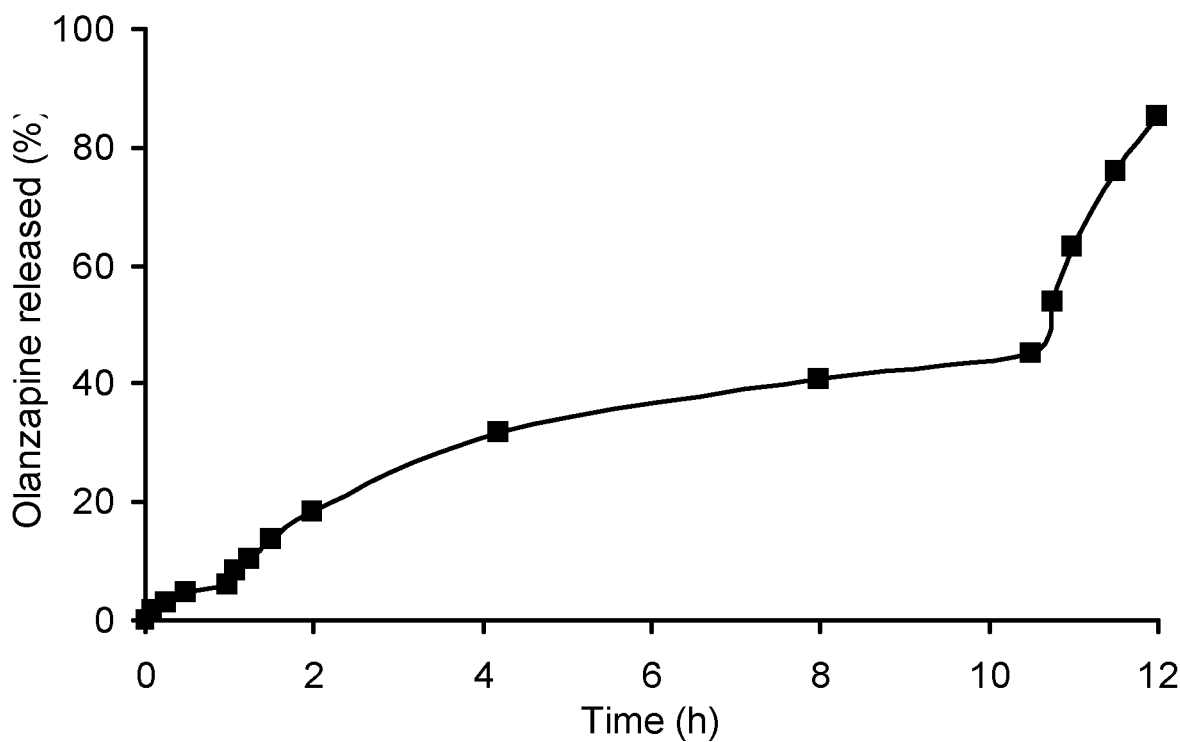
FIG. 12 shows the dissolution profile of coated olanzapine drug resin complex (OzDRC) obtained in Example 5D (USP method #2, paddle rotation speed 75 rpm, 37° C., dissolution medium 0-1 h: 500 ml 0.1 N HCl, 1-12 h: buffer mixture [500 ml 0.1 N HCl+500 ml phosphate buffer], pH 5.6, ionic strength 0.075; 10 g of NaCl was added after 10.5 h).

Dissolution profiles of coated drug resin complexes obtained in Examples 3D, 4D and 5D are shown in FIGS. 10 to 12.

The invention claimed is:

1. Oral pharmaceutical composition comprising coated particles of a complex of at least one active agent with an ion-exchange resin, wherein said particles are coated with a bioadhesive coating layer comprising at least one bioadhesive material and wherein the coated particles further comprise an enteric coating layer which is placed over the bioadhesive layer and comprises at least one enteric coating material, and at least a portion of the coated particles further comprises a release modifying coating layer which is placed between the complex and the bioadhesive layer and comprises at least one release modifying material, wherein the bioadhesive material is selected from the group consisting of homopolymers of acrylic acid or an alkylacrylic acid, crosslinked homopolymers of acrylic acid or an alkylacrylic acid, copolymers of acrylic acid or methacrylic acid with a $(C_{10}-C_{30})$alkyl acrylate, and crosslinked copolymers of acrylic or methacrylic acid with a $(C_{10-30})$alkyl acrylate.

2. The composition according to claim 1, wherein the bioadhesive material has a weight average molecular weight of at least about 10,000 Daltons.

3. The composition according to claim 1, wherein the enteric coating material is selected from the group consisting of anionic cellulose derivatives, anionic vinyl resins and anionic acrylic resins.

4. The composition according to claim 3, wherein the enteric coating material is selected from the group consisting of cellulose acetate phthalate, cellulose diacetate phthalate, cellulose triacetate phthalate, methylcellulose phthalate, hydroxypropyl cellulose phthalate, hydroxypropyl methylcellulose phthalate, cellulose acetate hexahydrophthalate, hydroxypropyl methylcellulose hexahydrophthalate, pharmaceutically acceptable salts thereof, polyvinyl acetate phthalate, poly(methacrylic acid-co-ethylacrylate) and poly(methacrylic acid-co-methylmethacrylate).

5. The composition according to claim 1, wherein the release modifying material is selected from delayed release materials and/or controlled release materials.

6. The composition according to claim 5, wherein the release modifying material is selected from the group consisting of ethyl cellulose, methyl cellulose, hydroxypropylmethylcellulose, cellulose acetate, cellulose acetate phthalate, cellulose acetate trimellitate, hydroxypropyl methylcellulose phthalate, hydroxypropyl methylcellulose acetate succinate, poly(methacrylic acid-co-ethylacrylate), poly(methacrylic acid-co-methylmethacrylate), polyvinylchloride, polyvinyl acetate phthalate, poly(vinylpyrrolidone-co-vinylacetate), silicone elastomers, shellac, zein, rosin esters and mixtures thereof.

7. The composition according to claim 6, wherein the release modifying material is selected from the group consisting of methyl cellulose, ethyl cellulose and mixtures thereof.

8. The composition according to claim 1 comprising at least two groups of coated particles differing in the amount and/or the composition of release modifying material.

9. The composition according to claim 1, wherein the ion exchange resin is selected from the group consisting of polymers of acrylic acid, copolymers of acrylic acid, polymers of methacrylic acid, copolymers of methacrylic acid, polymers of styrene modified with ionic groups, copolymers of styrene modified with ionic groups, cellulose modified with ionic groups, dextran modified with ionic groups and silica gel modified with ionic groups, wherein said ionic groups are selected from sulfonate groups, tertiary amine groups and quaternary ammonium groups.

10. The composition according to claim 1, wherein the ion exchange resin is a crosslinked sulfonated copolymer of styrene and divinylbenzene.

11. The composition according to claim 1, wherein the average particle size of the particles of the complex of the active agent with the ion-exchange resin is about 10 to about 3000 μm.

12. The composition according to claim 1, wherein the average particle size of the coated particles is about 20 to about 5000 μm.

13. The composition according to claim 1, wherein the coated particles have a specific gravity in the range from 1.1 to 2.0.

14. The composition according to claim 1, wherein the coated particles exhibit a specific surface area in the range of from about 1 to 200 m$^2$/g.

15. The composition according to claim 1, wherein the active agent is selected from the group consisting of ondansetron, granisetron, tropisetron, dolasetron, palonosetron, aprepitant, sulfasalazine, doxazosin, atenolol, bisoprolol, hydrochlorothiazide, carvedilol, amlodipine, felodipine, nifedipine, verapamil, diltiazem, enalapril, lisinopril, ramipril, quinapril, cilazapril, fosinopril, trandolapril, losartan, valsartan, simvastatin, lovastatin, fluvastatin, atorvastatin, rosuvastatin, gemfibrozil, fenofibrate, cholestyramine, oxybutynin, propiverine, solifenacin, trospium, darifenacin, sildenafil, phentolamine, tamsulosin, finasteride, cyclophosphamide, chlorambucil, melphalan, busulfan, lomustin, temozolomide, methotrexate, mercaptopurine, thioguanine, cladribine, fludarabine, cytarabine, 5-fluorouracil, gemcitabine, capecitabine, vinblastine, vincristine, vindesine, etoposide, paclitaxel, docetaxel, actinomycin D, doxorubicin, daunorubicin, epirubicin, idarubicin, mitoxantrone, bleo-mycin, mitomycin, cisplatin, carboplatin, oxaliplatin, procarbazine, rituximab, trastuzumab, cetuximab, bevacizumab, sunitinib, sorafenib, dasatinib, lapatinib, nilotinib, temsirolimus, amsacrine, asparaginase, hydroxyurea, estramustine, topotecan, irinotecan, imatinib, bortezomib, erlotinib, anagrelide, megestrol, tamoxifen, flutamide, nilutamide, bicalutamide, anastrazole, letrozole, exemestane, mycophenolate mofetil, sirolimus, everolimus, cyclosporine, tacrolimus, azathioprine, etidronic acid, clodronic acid, pamidronic acid, alendronic acid, tiludronic acid, ibandronic acid, risedronic acid, zoledronic acid, morphine, hydromorphone, oxycodone, pethidine, fentanyl, pentazocine, buprenorphine, tramadol, acetylsalicylic acid, metamizole, paracetamol, sumatriptan, methylphenobarbital, phenobarbital, primidone, phenytoin, ethosuximide, clonazepam, carbamazepine, oxcarbazepine, valproic acid, vigabatrin, progabide, tiagabine, sultiame, phenacemide, lamotrigine, felbamate, topiramate, gabapentin, pheneturide, levetiracetam, zonisamide, pregabalin, stiripentol, lacosamide, beclamide, trihexyphenidyl, biperiden, levodopa, carbidopa, benserazide, entacapone, amantadine, bromocriptine, pergolide, dihydroergocryptine, ropinirole, pramipexole, cabergoline, apomorphine, piribedil, rotigotine, selegiline, rasagiline, tolcapone, entacapone, budipine, levomepromazine, chlorpromazine, promazine, fluphenazine, perazine, haloperidol, sertindole, ziprazidone, zuclopenthixol, clozapine, olanzapine, quetiapine, loxapine, sulpiride, amisulpride, lithium, prothipendyl, risperidone, clotiapine, mosapramine, zotepine, aripiprazole, paliperidone, diazepam, alprazolam, meprobamate, flurazepam, nitrazepam, midazolam, zolpidem, clomipramine, amitriptyline, maprotiline, fluoxetine, citalopram, paroxetine, sertraline, alaproclate, fluvoxamine, etoperidon, escitalopram, mirtazapine, venlafaxine, methylphenidate, modafinil, neostigmine, pyridostigmine, disulfiram, naloxone, methadone, riluzole, abacavir, aciclovir, atropine, buspirone, caffeine, captopril, chloroquine, chlorphenamine, desipramine, diphenhydramine, disopyramide, doxepin, doxycycline, ephedrine, ergonovine, ethambutol, glucose, imipramine, ketorolac, ketoprofen, labetalol, levofloxacin, metoprolol, metronidazole, minocycline, misoprostol, phenazone, phenylalanine, prednisolone, primaquine, propranolol, quinidine, rosiglitazone, salicylic acid, theophylline, zidovudine, codeine, dextromethorphan, hydrocodone, hydralazine, metaproterenol, phenylpropanolamine, pseudoephedrine and mixtures thereof.

16. The composition according to claim 15, wherein the active agent is selected from the group consisting of levodopa, carbidopa, benserazide, entacapone and mixtures thereof.

17. The composition according to claim 15, wherein the active agent is selected from the group consisting of alendronate, olanzapine, risperidone and ropinirole.

18. The composition according to claim 1 comprising at least two groups of coated particles comprising different active agents.

19. The composition according to claim 1 further comprising an active agent, or a pharmaceutically acceptable salt or solvate thereof, outside the coated particles.

20. The composition according to claim 16 comprising levodopa and carbidopa or benserazide in a ratio of 20:1 to 1:1.

21. The composition according to claim 1, wherein the coated particles comprise
(a) 1 to 50 wt. % of said at least one active agent;
(b) 1 to 50 wt. % of said ion-exchange resin;
(c) 1 to 50 wt. % of release modifying material;
(d) 0.5 to 30 wt. % of said bioadhesive material; and
(e) 1 to 80 wt. % of said enteric coating material;
based on the total weight of the coated particles.

22. Process for preparing a composition according to claim 1, said process comprising the steps of:
(i) contacting an active agent with an ion-exchange resin to obtain an active agent/ion exchange resin complex;
(ii) coating the complex of step (i) with a coating layer comprising a release modifying material;
(iii) coating the coated complex of step (ii) with a coating layer comprising a bioadhesive material; and
(iv) coating the coated complex of step (iii) with a coating layer comprising an enteric coating material.

23. The composition according to claim 1, wherein the enteric coating layer is placed directly over the bioadhesive layer.

24. The composition according to claim 2, wherein the enteric coating layer is placed directly over the bioadhesive layer.

25. The composition according to claim 1, wherein the bioadhesive material is selected from the group consisting of homopolymers of acrylic acid, homopolymers of alkylacrylic acid, crosslinked homopolymers of acrylic acid and crosslinked homopolymers of alkylacrylic acid.

* * * * *